US010556855B1

(12) United States Patent
Angel et al.

(10) Patent No.: US 10,556,855 B1
(45) Date of Patent: *Feb. 11, 2020

(54) CATIONIC LIPIDS AND TRANSFECTION METHODS

(71) Applicant: Factor Bioscience Inc., Cambridge, MA (US)

(72) Inventors: Matthew Angel, Cambridge, MA (US); Franklin Kostas, Cambridge, MA (US); Christopher Rohde, Cambridge, MA (US)

(73) Assignee: Factor Bioscience Inc., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/660,299

(22) Filed: Oct. 22, 2019

Related U.S. Application Data

(63) Continuation of application No. 16/526,621, filed on Jul. 30, 2019, now Pat. No. 10,501,404.

(51) Int. Cl.
*C07C 215/24* (2006.01)
*A61K 9/127* (2006.01)

(52) U.S. Cl.
CPC .......... *C07C 215/24* (2013.01); *A61K 9/1272* (2013.01)

(58) Field of Classification Search
None
See application file for complete search history.

(56) References Cited

U.S. PATENT DOCUMENTS

| | | | |
|---|---|---|---|
| 3,539,465 A | 11/1970 | Jensen et al. |
| 5,837,533 A | 11/1998 | Boutin |
| 5,843,780 A | 12/1998 | Thomson |
| 6,127,170 A | 10/2000 | Boutin |
| 6,379,965 B1 | 4/2002 | Boutin |
| 6,835,712 B1 | 12/2004 | Camilleri et al. |
| 7,145,039 B2 | 12/2006 | Chu et al. |
| 7,166,745 B1 | 1/2007 | Chu et al. |
| 7,173,154 B2 | 2/2007 | Chu et al. |
| 7,276,489 B2 | 10/2007 | Agrawal et al. |
| 7,323,594 B2 | 1/2008 | Chu et al. |
| 7,442,548 B2 | 10/2008 | Thomson et al. |
| 7,449,334 B2 | 11/2008 | Thomson et al. |
| 7,470,817 B2 | 12/2008 | Chu et al. |
| 7,479,573 B2 | 1/2009 | Chu et al. |
| 7,601,872 B2 | 10/2009 | Chu et al. |
| 7,621,606 B2 | 11/2009 | Page et al. |
| 7,682,828 B2 | 3/2010 | Jaenisch et al. |
| 7,687,266 B2 | 3/2010 | Chambers et al. |
| 7,812,000 B2 | 10/2010 | Agrawal et al. |
| 7,915,450 B2 | 3/2011 | Chu et al. |
| 8,048,675 B1 | 11/2011 | Irion |
| 8,048,999 B2 | 11/2011 | Yamanaka et al. |
| 8,058,065 B2 | 11/2011 | Yamanaka et al. |
| 8,071,369 B2 | 12/2011 | Jaenisch et al. |
| 8,129,187 B2 | 3/2012 | Yamanaka et al. |
| 8,129,348 B2 | 3/2012 | Besman et al. |
| 8,158,827 B2 | 4/2012 | Chu et al. |
| 8,202,850 B2 | 6/2012 | Agrawal et al. |
| 8,278,036 B2 | 10/2012 | Kariko et al. |
| 8,420,782 B2 | 4/2013 | Bonas et al. |
| 8,440,431 B2 | 5/2013 | Voytas et al. |
| 8,440,432 B2 | 5/2013 | Voytas et al. |
| 8,450,471 B2 | 5/2013 | Voytas et al. |
| 8,470,973 B2 | 6/2013 | Bonas et al. |
| 8,497,124 B2 | 7/2013 | Angel et al. |
| 8,586,526 B2 | 11/2013 | Gregory et al. |
| 8,685,737 B2 | 4/2014 | Serber et al. |
| 8,691,966 B2 | 4/2014 | Kariko et al. |
| 8,710,200 B2 | 4/2014 | Schrum et al. |
| 8,716,465 B2 | 5/2014 | Rossi et al. |
| 8,748,089 B2 | 6/2014 | Kariko et al. |
| 8,785,200 B2 | 7/2014 | Chu et al. |
| 8,802,438 B2 | 8/2014 | Rossi et al. |
| 8,822,663 B2 | 9/2014 | Schrum et al. |
| 8,835,108 B2 | 9/2014 | Kariko et al. |
| 8,883,506 B2 | 11/2014 | Rossi et al. |
| 9,127,248 B2 | 9/2015 | Angel et al. |
| 9,358,300 B2 | 6/2016 | Chu et al. |
| 9,376,669 B2 | 6/2016 | Angel et al. |
| 9,399,761 B2 | 7/2016 | Angel et al. |
| 9,422,577 B2 | 8/2016 | Angel et al. |
| 9,447,395 B2 | 9/2016 | Angel et al. |
| 9,464,285 B2 | 10/2016 | Angel et al. |
| 9,487,768 B2 | 11/2016 | Angel et al. |
| 9,562,218 B2 | 2/2017 | Angel et al. |
| 9,597,357 B2 | 3/2017 | Gregory et al. |
| 9,605,277 B2 | 3/2017 | Angel et al. |
| 9,605,278 B2 | 3/2017 | Angel et al. |

(Continued)

FOREIGN PATENT DOCUMENTS

CN 101200758 6/2008
EP 2241572 A2 10/2010

(Continued)

OTHER PUBLICATIONS

Akinc, et al., "A combinatorial library of lipid-like materials for delivery of RNAi therapeutics," Nature Biotechnology, 26(5): May 2008, pp. 561-569.

Alabi, et al., "A combinatorial library of lipid-like materials for delivery of RNAi therapeutics," Nat Biotechnol., 26(5), May 2008, pp. 561-569.

Albumax I product insert, Invitrogen Corporation, 1 page (2001).

Ambegia, et al., "Stabilized plasmid-lipid particles containing PEG-diacylglycerols exhibit extended circulation lifetimes and tumor selective gene expression," Biochimica et Biophysica Acta (BBA)—Biomembranes, 169, 2005, pp. 155-163.

(Continued)

*Primary Examiner* — Brian J Davis

(74) *Attorney, Agent, or Firm* — Morgan, Lewis & Bockius LLP

(57) ABSTRACT

The present invention relates in part to novel cationic lipids and their use, e.g., in delivering nucleic acids to cells.

30 Claims, 12 Drawing Sheets

(56) References Cited

U.S. PATENT DOCUMENTS

| | | |
|---|---|---|
| 9,657,282 B2 | 5/2017 | Angel et al. |
| 9,695,401 B2 | 7/2017 | Angel et al. |
| 9,758,797 B2 | 9/2017 | Angel et al. |
| 9,770,489 B2 | 9/2017 | Angel et al. |
| 9,879,228 B2 | 1/2018 | Angel et al. |
| 9,969,983 B2 | 5/2018 | Angel et al. |
| 10,124,042 B2 | 11/2018 | Angel et al. |
| 10,131,882 B2 | 11/2018 | Angel et al. |
| 10,137,206 B2 | 11/2018 | Angel et al. |
| 10,195,280 B2 | 2/2019 | de Mollerat du Jeu et al. |
| 10,301,599 B2 | 5/2019 | Angel et al. |
| 10,350,304 B2 | 7/2019 | Angel et al. |
| 10,363,321 B2 | 7/2019 | Angel et al. |
| 2003/0009148 A1 | 1/2003 | Hayakawa |
| 2003/0083272 A1 | 5/2003 | Wiederholt et al. |
| 2003/0228658 A1 | 12/2003 | Shu et al. |
| 2005/0053588 A1 | 3/2005 | Yin |
| 2005/0130144 A1 | 6/2005 | Nakatsuji et al. |
| 2005/0192357 A1 | 9/2005 | Arai et al. |
| 2005/0272634 A1 | 12/2005 | Bahlmann et al. |
| 2007/0134796 A1 | 6/2007 | Holmes et al. |
| 2008/0009785 A1 | 1/2008 | Mikszta et al. |
| 2008/0213377 A1 | 9/2008 | Bhatia et al. |
| 2008/0233610 A1 | 9/2008 | Thomson et al. |
| 2008/0260706 A1 | 10/2008 | Rabinovich et al. |
| 2009/0029465 A1 | 1/2009 | Thomson et al. |
| 2009/0093433 A1 | 4/2009 | Woolf et al. |
| 2009/0275128 A1 | 11/2009 | Thomson et al. |
| 2009/0286852 A1 | 11/2009 | Kariko et al. |
| 2010/0003757 A1 | 1/2010 | MacK et al. |
| 2010/0047261 A1 | 2/2010 | Hoerr et al. |
| 2010/0075421 A1 | 3/2010 | Yamanka et al. |
| 2010/0076057 A1 | 3/2010 | Sontheimer et al. |
| 2010/0120079 A1 | 5/2010 | Page et al. |
| 2010/0144031 A1 | 6/2010 | Jaenisch et al. |
| 2010/0167286 A1 | 7/2010 | Reijo Pera et al. |
| 2010/0168000 A1 | 7/2010 | Kiessling et al. |
| 2010/0172882 A1 | 7/2010 | Glazer et al. |
| 2010/0184033 A1 | 7/2010 | West et al. |
| 2010/0184227 A1 | 7/2010 | Thomson et al. |
| 2010/0221829 A1 | 9/2010 | Amit et al. |
| 2010/0233804 A1 | 9/2010 | Zhou et al. |
| 2010/0267141 A1 | 10/2010 | Shi et al. |
| 2010/0272695 A1 | 10/2010 | Agulnick et al. |
| 2010/0273220 A1 | 10/2010 | Yanki et al. |
| 2010/0304481 A1 | 12/2010 | Thomson et al. |
| 2010/0311171 A1 | 12/2010 | Nakanishi et al. |
| 2010/0317104 A1 | 12/2010 | Elefanty et al. |
| 2011/0045001 A1 | 2/2011 | Klosel et al. |
| 2011/0065103 A1 | 3/2011 | Sahin et al. |
| 2011/0076678 A1 | 3/2011 | Jaenisch et al. |
| 2011/0104125 A1 | 5/2011 | Yu |
| 2011/0110899 A1 | 5/2011 | Shi et al. |
| 2011/0143397 A1 | 6/2011 | Kariko et al. |
| 2011/0143436 A1 | 6/2011 | Dahl et al. |
| 2011/0145940 A1 | 6/2011 | Voytas et al. |
| 2011/0151557 A1 | 6/2011 | Reh et al. |
| 2011/0165133 A1 | 7/2011 | Rabinovich et al. |
| 2011/0171185 A1 | 7/2011 | Klimanskaya et al. |
| 2011/0189137 A1 | 8/2011 | Rana et al. |
| 2011/0213335 A1 | 9/2011 | Burton et al. |
| 2011/0236978 A1 | 9/2011 | Stolzing et al. |
| 2011/0239315 A1 | 9/2011 | Bonas et al. |
| 2011/0244566 A1 | 10/2011 | Wu et al. |
| 2011/0263015 A1 | 10/2011 | D'Costa et al. |
| 2011/0301073 A1 | 12/2011 | Gregory et al. |
| 2012/0046346 A1 | 2/2012 | Rossi et al. |
| 2012/0064620 A1 | 3/2012 | Bonas et al. |
| 2012/0192301 A1 | 7/2012 | Jaenisch et al. |
| 2012/0195936 A1 | 8/2012 | Rudolph et al. |
| 2012/0202291 A1 | 8/2012 | Chen et al. |
| 2012/0208278 A1 | 8/2012 | Yanik et al. |
| 2012/0237975 A1 | 9/2012 | Schrum et al. |
| 2012/0301455 A1 | 11/2012 | Hunt |
| 2013/0040302 A1 | 2/2013 | Burke et al. |
| 2013/0071365 A1 | 3/2013 | Suzuki |
| 2013/0102034 A1 | 4/2013 | Schrum |
| 2013/0115272 A1 | 5/2013 | de Fougerolles et al. |
| 2013/0122581 A1 | 5/2013 | Voytas et al. |
| 2013/0123481 A1 | 5/2013 | de Fougerolles et al. |
| 2013/0156849 A1 | 6/2013 | de Fougerolles et al. |
| 2013/0165504 A1 | 6/2013 | Bancel et al. |
| 2013/0189327 A1 | 7/2013 | Ortega et al. |
| 2013/0189741 A1 | 7/2013 | Meis et al. |
| 2013/0203115 A1 | 8/2013 | Schrum et al. |
| 2013/0217119 A1 | 8/2013 | Bonas et al. |
| 2013/0244282 A1 | 9/2013 | Schrum et al. |
| 2013/0245103 A1 | 9/2013 | de Fougerolles et al. |
| 2013/0274129 A1 | 10/2013 | Katzen et al. |
| 2013/0302295 A1 | 11/2013 | Wang et al. |
| 2013/0345274 A1 | 12/2013 | Father |
| 2014/0073053 A1 | 3/2014 | Yanik et al. |
| 2014/0073687 A1 | 3/2014 | Chien et al. |
| 2014/0127814 A1 | 5/2014 | Chandrasegaran et al. |
| 2014/0194482 A1 | 7/2014 | Father et al. |
| 2014/0242154 A1 | 8/2014 | Ramunas et al. |
| 2014/0242155 A1 | 8/2014 | Ramunas et al. |
| 2014/0242595 A1 | 8/2014 | Yu et al. |
| 2014/0315988 A1 | 10/2014 | Dahl et al. |
| 2014/0349401 A1 | 11/2014 | Wang |
| 2014/0356906 A1 | 12/2014 | Angel et al. |
| 2015/0275193 A1 | 10/2015 | Angel et al. |
| 2016/0045600 A1 | 2/2016 | de Mollerat du Jeu et al. |
| 2016/0185681 A1 | 6/2016 | Fabry |

FOREIGN PATENT DOCUMENTS

| | | |
|---|---|---|
| EP | 2272961 A1 | 1/2011 |
| EP | 2320952 B1 | 5/2011 |
| JP | 2003306448 | 10/2003 |
| JP | 2010246551 | 11/2010 |
| JP | 2011160661 | 8/2011 |
| WO | WO 96/10038 | 4/1996 |
| WO | WO 97/42819 | 11/1997 |
| WO | WO 98/00551 | 1/1998 |
| WO | WO 98/30679 | 7/1998 |
| WO | WO 00/12454 | 3/2000 |
| WO | WO 00/27795 | 5/2000 |
| WO | WO 00/74763 A2 | 12/2000 |
| WO | WO 00/77032 A2 | 12/2000 |
| WO | WO 02/26757 A2 | 4/2002 |
| WO | WO 02/094251 A1 | 11/2002 |
| WO | WO 03/086472 A1 | 4/2003 |
| WO | WO 2007/006808 A1 | 1/2007 |
| WO | WO 2007/024708 A2 | 3/2007 |
| WO | WO 2008/065381 A1 | 6/2008 |
| WO | WO 2009/006930 A1 | 1/2009 |
| WO | WO 2009/077134 A2 | 6/2009 |
| WO | WO 2009/127230 A1 | 10/2009 |
| WO | WO 2009/147400 A1 | 12/2009 |
| WO | WO 2010/012472 A1 | 2/2010 |
| WO | WO 2010/093655 A2 | 8/2010 |
| WO | WO 2010/123501 A1 | 10/2010 |
| WO | WO 2010/130447 A1 | 11/2010 |
| WO | WO 2010/148050 A2 | 12/2010 |
| WO | WO 2011/012316 A2 | 2/2011 |
| WO | WO 2011/134210 A1 | 3/2011 |
| WO | WO 2011/071931 A2 | 6/2011 |
| WO | WO 2011/071936 A2 | 6/2011 |
| WO | WO 2011/072246 A2 | 6/2011 |
| WO | WO 2011/110886 A1 | 9/2011 |
| WO | WO 2011/114237 A2 | 9/2011 |
| WO | WO 2011/130624 A2 | 10/2011 |
| WO | WO 2011/140397 A2 | 11/2011 |
| WO | WO 2011/141820 A1 | 11/2011 |
| WO | WO 2011/146121 A1 | 11/2011 |
| WO | WO 2011/154393 A1 | 12/2011 |
| WO | WO 2011/159369 A1 | 12/2011 |
| WO | WO 2012/019122 A2 | 2/2012 |
| WO | WO 2012/019168 A2 | 2/2012 |
| WO | WO 2012/036299 A1 | 3/2012 |
| WO | WO 2012/048213 A1 | 4/2012 |
| WO | WO 2012/060473 A1 | 5/2012 |
| WO | WO 2012/122318 A2 | 9/2012 |

(56) References Cited

FOREIGN PATENT DOCUMENTS

| | | |
|---|---|---|
| WO | WO 2012/131090 A1 | 10/2012 |
| WO | WO 2012/138453 A1 | 10/2012 |
| WO | WO 2012/138939 A1 | 10/2012 |
| WO | WO 2012/174224 A2 | 12/2012 |
| WO | WO 2012/176015 A1 | 12/2012 |
| WO | WO 2013/003475 A1 | 1/2013 |
| WO | WO 2013/020064 A1 | 2/2013 |
| WO | WO 2013/053819 A1 | 4/2013 |
| WO | WO 2013/078199 A2 | 5/2013 |
| WO | WO 2013/086008 A1 | 6/2013 |
| WO | WO 2013/102203 A1 | 7/2013 |
| WO | WO 2013/151671 A1 | 10/2013 |
| WO | WO 2013/163296 A1 | 10/2013 |
| WO | WO 2013/173248 A2 | 11/2013 |
| WO | WO 2014/015314 A1 | 1/2014 |
| WO | WO 2014/071219 A1 | 5/2014 |
| WO | WO 2014/134412 A1 | 9/2014 |
| WO | WO 2014/190361 A2 | 11/2014 |
| WO | WO 2015/038075 A1 | 3/2015 |
| WO | WO 2015/117021 A1 | 8/2015 |
| WO | WO 2016/011203 A1 | 1/2016 |
| WO | WO 2016/131052 A1 | 8/2016 |
| WO | WO 2017/152015 A1 | 9/2017 |
| WO | WO 2018/035377 A1 | 2/2018 |
| WO | WO 2018/064584 A1 | 4/2018 |
| WO | WO 2019/045897 A1 | 3/2019 |

OTHER PUBLICATIONS

Anderson, et al., "Incorporation of pseudouridine into mRNA enhances translation by diminishing PKR activation," Nucl. Acids Res. 38(17): 5884-5892 (2010).

Anderson, et al., "Nucleofection induces transient eiF2a phosphorylation by GCN2 and PERK," Gene Ther., pp. 1-7 (2012).

Anderson, et al., "Nucleoside modifications in RNA limit activation of 2'-5'-oligoadenylate synthetase and increase resistance to cleavage by RNase L," Nucl. Acids Res. 39(21):9329-9338 (2011).

Angel, et al., "Innate Immune Suppression Enables Frequent Transfection with RNA Encoding Reprogramming Proteins," PLoS One, vol. 5(7), e11756, pp. 1-7 (2010).

Angel, "Extended Transient Transfection by Repeated Delivery of an in Vitro-Transcribed RNA," Master of Science in Electrical Engineering and Computer Science, 56 pages (Massachusetts Institute of Technology, Cambridge, Massachusetts;) (2009).

Angel, "Reprogramming Human Somatic Cells to Pluripotency Using RNA", pp. 1-89 (Ph.D. diss., Massachusetts Institute of Technology) (2012).

Angel, "Reprogramming human somatic cells to pluripotency using RNA," Doctor of Philosophy in Electrical Engineering and Computer Science, 55 pages (Massachusetts Institute of Technology, Cambridge, Massachusetts;) (2011).

Arnold, et al., "Reprogramming of Human Huntington Fibroblasts Using mRNA," ISRN Cell Biology 2012: Article ID 124878, pp. 1-12 (2012).

Ball, et al., "Achieving long-term stability of lipid nanparticles: examining the effect of pH, temperature, and lyophilization," International Journal of Nanomedicine, 12, 2017, pp. 305-315.

Ball, et al., "Lipid Nanoparticle Formulations for Enhanced Co-delivery of siRNA and mRNA," Nano Lett. 18, 2018, pp. 3814-3822.

Barker, et al., "A method for the deionization of bovine serum albumin," Tissue Culture Association, pp. 111-112 (1975).

Berg, "Proposed structure for the zinc-binding domains from transcription factor IIIA and related proteins," Proc. Natl. Acad. Sci. USA, vol. 85, pp. 99-102 (1988).

Boch, et al., "Breaking the Code of DNA Binding Specificity of TAL-Type III Effectors," Science, vol. 3126, pp. 1509-1512 (2009).

Bogdanove, et al., "TAL effectors: customizable proteins for DNA targeting", Science, vol. 333, pp. 1843-1846 (2011).

Bolli, et al., "Cardiac stem cells in patients with ischaemic cardiomyopathy (SCIPIO): initial results of a randomized phase 1 trial," Lancet 378:1847-1857 (2011).

Braam, et al., "Recombinant vitronectin is a functionally defined substrate that supports human embryonic stem cell self-renewal via αv β5 integrin," Stem Cells 26:2257-2265 (2008).

Carroll, "Progress and prospects: Zinc-finger nucleases as gene therapy agents," Gene Therapy, vol. 15, pp. 1463-1468 (2008).

Chan, et al., "Optimizing Cationic and Neutral Lipids for Efficient Gene Delivery at High Serum Content," J Gene Medicine, 16(0), Mar. 2014, pp. 84-96.

Chen, et al., "Chemically defined conditions for human iPSC derivation and culture," Nat. Methods 8:424-429 (2011).

Chen, et al., "Metastasis is regulated via microRNA-200/ZEB1 axis control of tumour cell PD-L1 expression and intratumoral immunosuppression," Nature Communications, Oct. 28, 2014, 5: 5241, pp. 1-12.

Chen, et al., "Rational optimization of reprogramming culture conditions for the generation of induced pluripotent stem cells with ultra-high efficiency and fast kinetics," Cell Research 21:884-894 (2011).

Chen, et al., "Role of MEF feeder cells in direct reprograming of mousetail-tip fibroblasts." Cell Biology International., vol. 33, No. 12., pp. 1268-1273 (2009).

Christian, et al., "Targeting DNA Double-Strand Breaks with TAL Effector Nucleases," Genetics, vol. 186, pp. 757-761 (2010).

Cox, et al, "Therapeutic Genome Editing: Prospects and Challenges." Nat Med., vol. 21, No. 2 pp. 121-131 (2015).

Cui, et al., "Targeted integration in rat and mouse embryos with zinc-finger nucleases," Nat. Biotech., vol. 29, No. 1, pp. 64-67 (2011).

Dang, et al., "Mutation analysis and characterization of COL7A1 mutations in dystrophic epidermolysis bullosa." Experimental Dermatology, 17, 553-568 (2008).

Davis, "Stabilization of RNA stacking by pseudouridine," Nucleic Acids Research, vol. 23, No. 24, pp. 5020-5026 (1995).

Deng, et al "Structural Basis for Sequence-Specific Recognition of DNA by TAL Effectors" Science. 335(6069) 720-723 (2012).

Droge, et al., "A comparative study of some physico-chemical properties of human serum albumin samples from different sources. Some physico-chemical properties of isoionic human serum albumin solutions," Biochem. Pharmacal. 31, 3775-3779 (1982).

Efe, et al., "Conversion of mouse fibroblasts into cardiomyocytes using a direct reprogramming strategy," Nat. Cell Biol. 13:215-222 (2011).

Fixe, "Tebu-Bio.com; Cas9 mRNA optimized for genome editing." https://www.tebu-bio.com/blog/2015/09/07/cas9-nnrna-optimized-for-genonne-editing/) (2015).

Fritsch, et al., "Dominant-negative Effects of COL7A1 Mutations Can be Rescued by Controlled Overexpression of Normal Collagen VII," The Journal of Biological Chemistry, vol. 284, No. 44, pp. 30248-30256, (2009).

Garcia-Gonzalo, et al., "Albumin-associated lipids regulate human embryonic stem cell self-renewal," PLoS One 3: e1384, 1-10 (2008).

Gardner, et al., "Synthesis and Transfection Efficiencies of New Lipophilic Polyamines," J. Med. Chem., 50, 2007, pp. 308-318.

Geall, et al., "Nonviral delivery of self-amplifying RNA vaccines," National Academy of Sciences, 109, Sep. 2012, pp. 14604-14609.

Geurts, et al., "Knockout Rats via Embryo Microinjection of Zinc-Finger Nucleases," Science, vol. 325, p. 433 (2009).

Ghonaim, et al., "Varying the Chain Length in $N^4$, $N^9$-Diacyl Spermines: Non-Viral Lipopolyamine Vectors for Efficient Plasmid DNA formulation," Mol. Pharmaceutics, 5, 2008, pp. 1111-1121.

Goldberg, et al., "The enzymatic synthesis of pseudouridine triphosphate," Biochim. Biophys. Acta, vol. 54, pp. 202-204 (1961).

Goldberg, et al., "The incorporation of 5-ribosyluracil triphosphate into RNA in nuclear extracts of mammalian cells," Biochem. Biophys. Res. Commun. 6, pp. 394-398 (1961).

Goldberg, "Ribonucleic acid synthesis in nuclear extracts of mammalian cells grown in suspension culture; effect of ionic strength and surface-active agents," Biochim. Biophys. Acta, vol. 51, pp. 201-204 (1961).

Goto, et al., "Fibroblasts Show More Potential as Target Cells than Keratinocytes in COL7A1 Gene Therapy of Dystrophic Epidermolysis Bullosa", Journal of Investigative Dermatology 126, 766-772 (2006).

(56) References Cited

OTHER PUBLICATIONS

Goto, et al., "Targeted Skipping of a Single Exon Harboring a Premature Termination Codon Mutation: Implications and Potential for Gene Correction Therapy for Selective Dystrophic Epidermolysis Bullosa Patients," Journal of Investigative Dermatology, vol. 126, pp. 2614-2620, (2006).
"Guidance Notes for the Safe Storage and Handling of Cryogenic Materials", Dec. 2002, pp. 1-32, especially p. 2, [online] Retrieved from the Internet: https://www.st-andrews.ac.uk/staff/policy/healthandsafety/publications/cryogenics-safestorageandhandling/.
Gurung, et al., "β-Catenin is a Mediator of the Response of Fibroblasts to Irradiation," The American Journal of Pathology, vol. 174, No. 1, pp. 248-255 (2009).
Hamanaka, et al., "Generation of Germline-Component Rat Induced Pluripotent Stem Cells," PlosOne, vol. 6, Issue 7, pp. 1-9 (2011).
Heyes, et al., "Cationic lipid saturation influences intracellular delivery of encapsulated nucleic acids," Journal of Controlled Release, 107, 2005, pp. 276-287.
Hoban, et al. "Correction of the sickle cell disease mutation in human hematopoietic stem/progenitor cells" Blood 125(17):2597-2604 (2015).
Hockemeyer, et al., "Efficient targeting of expressed and silent genes in human ESCs and iPSCs using zinc-finger nucleases," Nature Biotechnology, vol. 27, No. 9, pp. 851-857 (2009).
Hockemeyer, et al.," Genetic engineering of human ES and iPS cells using TALE nucleases," Author Manuscript, available in PMC Feb. 1, 2012. Published in final edited form as: Nat Biotechnol. 29(8): 731-734 (2012).
Jayaraman, et al., "Maximizing the Potency of siRNA Lipid Nanoparticles for Hepatic Gene Silencing in Vivo," Angewandte Chemie International Edition, 51, 2012, pp. 8529-8533.
Juillerat, et al., "Optimized tuning of TALEN specificity using non-conventional RVDs", Sci. Rep., vol. 5:8150, pp. 1-7 (2015).
Kahan, et al., "The Role of Deoxyribonucleic Acid in Ribonucleic Acid Synthesis," The Journal of Biological Chemistry, vol. 237, No. 12, pp. 3778-3785 (1962).
Kariko, et al., "Generating the optimal mRNA for therapy: HPLC purification eliminates immune activation and improves translation of nucleoside-modified, protein-encoding mRNA," Nucl. Acids Res. 39:e142 (2011).
Kariko, et al., "In vivo protein expression from mRNA delivered into adult rat brain," J. Neurosci. Methods 105:77-86 (2001).
Kariko, et al., "Incorporation of pseudouridine into mRNA yields superior nonimmunogenic vector with increased translational capacity and biological stability," Mol. Ther. 16:1833-1840 (2008).
Kariko, et al., "Increased Erythropoiesis in Mice Injected with Sub-Microgram Quantities of Pseudouridine-containing mRNA Encoding Erythropoietin," Mol. Ther. 20:948-953 (2012).
Kariko, et al., "mRNA is an endogenous ligand for Toll-like receptor 3," J. Biol. Chem. 279, pp. 12542-12550 (2004).
Kariko, et al., "Naturally occurring nucleoside modifications suppress the immunostimulatory activity of RNA: implication for therapeutic RNA development," Drug Discovery & Development, vol. 10, No. 5, pp. 523-532 (2007).
Kariko, et al., "Suppression of RNA recognition by Toll-like receptors: the impact of nucleoside modification and the evolutionary origin of RNA," Immunity 23:165-175 (2005).
Kauffman, et al., "Optimization of Lipid Nanoparticle Formulations for mRNA Delivery in vivo with Fractional Factorial and Definitive Screening Designs," Nano Letters, 15, 2015, pp. 7300-7306.
Kawamata, et al., "Generation of genetically modified rats from embryonic stem cells," PNAS, vol. 107, No. 32, pp. 14223-14228 (2010).
Kern, et al., "Mechanisms of Fibroblast Cell Therapy for Dystrophic Epidermolysis Bullosa: High Stability of Collagen VII Favors Long-term Skin Integrity," Molecular Therapy, vol. 17, No. 9, 1605-1615, (2009).
Kim, et al., "Direct reprogramming of human neural stem cells by OCT4," Nature 461:649-653 (2009).
Kim, et al., "Generation of Human Induced Pluripotent Stem Cells by Direct Delivery of Reprogramming Proteins," Cell Stem Cell 4, pp. 472-476 (2009).
Kim, et al., "Hybrid restriction enzymes: Zinc finger fusions to Fok I cleavage domain," Proc. Natl. Acad. Sci. USA, vol. 93, pp. 1156-1160 (1996).
Kim, et al., "Oct4-induced pluripotency in adult neural stem cells," Cell 136:411-419 (2009).
Kim, et al., "Pluripotent stem cells induced from adult neural stem cells by reprogramming with two factors," Nature 454:646-650 (2008).
Kita, K. et al., "Overproduction and characterization of the StsI restriction endonuclease", Gene, vol. 169, pp. 69-73 (1996).
Krug, et al, "A GMP-compliant protocol to expand and transfect cancer patient T cells with mRNA encoding a tumor-specific chimeric antigen receptor." Cancer Immunol Immunother., pp. 1-10 (2014).
Kulkarni, et al., "Design of lipid nanoparticles for in vitro and in vivo delivery of plasmid DNA," Nanomedicine: Nanotechnology, Biology and Medicine 13, 2017, pp. 1377-1387.
Kulkarni, et al., "On the Formation and Morphology of Lipid Nanoparticles Containing Ionizable Cationic Lipids and siRNA," ACS Nano, 12, 2018, pp. 4787-4795.
Labas, et al., "Nature as a source of inspiration for cationic lipid synthesis," Genetica, 13, 2010, pp. 153-168.
Lee, et al., "Activation of Innate Immunity is Required for Efficient Nuclear Reprogramming," Cell 151,547-558 (2012).
Li, et al., "Effects of Chemically Modified Messenger RNA on Protein Expression," Bioconjugate Chem., Feb. 24, 2016, 27: pp. 849-853.
Li, et al., "Identification and characterization of mitochondrial targeting sequence of human apurinic/apyrimidinic endonuclease 1." Journal of Biological Chemistry, 285(20): 14871-14881 (2010).
Li, et al., "A biomimetic lipid library for gene delivery through thiol-yne click chemistry," Biomaterials 33, 2012, pp. 8160-8166.
Lin, et al., "A chemical platform for improved induction of human iPSCs," Nature Methods, vol. 6, No. 11, 805-808 (2009).
Product manual for Lipofectamine 2000 transfection reagent, Protocol Pub. No. MAN0007824 Rev.1.0, Thermo Fisher Scientific, Jun. 12, 2013 (https://assets.thermofisher.com/TFS-Assets/LSG/manuals/Lipofectamine_2000_Reag_protocol.pdf/ Accessed Oct. 22, 2019).
Product manual for Lipofectamine 3000 transfection reagent, Protocol Pub. No. MAN0009872 Rev.C.0, Invitrogen by Life Technologies, Thermo Fisher Scientific, Feb. 10, 2016 (https://www.thermofisher.com/content/dam/LifeTech/Documents/PDFs/lipofectamine3000_protocol.pdf/ Accessed Oct. 22, 2019).
Liu, et al., "A Small-Molecule Agonist of the Wnt Signaling Pathway," Angew. Chem. Int. Ed. 44, pp. 1987-1990 (2005).
Love, et al., "Lipid-like materials for low-dose, in vivo gene silencing," PNAS, vol. 107, No. 5, 2010, pp. 1864-1869.
Lu, et al. "Defined culture conditions of human embryonic stem cells" PNAS, 103, 5688-5693, (2006).
Ludwig, et al., "Derivation of human embryonic stem cells in defined conditions," Nat. Biotechnol. 24:185-187 (2006).
Ludwig, et al., "Feeder-independent culture of human embryonic stem cells," Nat. Methods 3:637-646 (2006).
Mahfouz, et al., "De novo-engineered transcription activator-like effector (TALE) hybrid nuclease with novel DNA binding specificity creates double-strand breaks," PNAS vol. 108, No. 6, pp. 2623-2628 (2011).
Mahon, et al., "A combinatorial approach to determine functional group effects on lipidoid-mediated siRNA delivery," Bioconjugate Chem, 21(8), Aug. 18, 2010, pp. 1448-1454.
Maier, et al., "Biodegradable Lipids Enabling Rapidly Eliminated Lipid Nanoparticles for Systemic Delivery of RNAi Therapeutics," The American Society of Gene & Cell Therapy, vol. 21, No. 8, Aug. 2013, pp. 1570-1578.
Maiti, et al., "Transfection efficiencies of α-tocopherylated cationic gemini lipids with hydroxyethyl bearing headgroups under high serum conditions," Org. Biomol. Che., 16, 2018, pp. 1983-1993.
Martinov, et al., "Fractioned radiotherapy combined with PD-1 pathway blockade promotes CD8 T cell-mediated tumor clearance

(56) References Cited

OTHER PUBLICATIONS for the treatment of advanced malignancies," Annals of Translational Medicine, Feb. 2016, 4(4): 82, pp. 1-4.
Mayr, et al., "Gene Therapy for the COL7A1 Gene" Open access peer-reviewed chapter. https://www.intechopen.com/books/gene-therapy-tools-and-potential-applications/gene-therapy-for-the-col7a1-gene Published Feb. 27, 2013.
Menger, et al. "TALEN-Mediated Inactivation of PD-1 in Tumor-Reactive Lymphocytes Promotes Intratumoral T-cell Persistence and Rejection of Established Tumors". Cancer Res; 76(8): 2087-2093. (2016).
Miller, et al., "A TALE nuclease architecture for efficient genome editing," Nature Biotechnology, vol. 29, No. 2, pp. 143-148 (2011).
Miller, et al., "An improved zinc-finger nuclease architecture for highly specific genome editing," Nat. Biotechnol.; vol. 25, No. 7, pp. 778-785 (2007).
Misra, et al., "Gene Transfection in High Serum Levels: Case Studies with New Cholesterol Based Cationic Gemini Lipids," PLOS One, vol. 8, No. 7, Jul. 2013, e68305.
Moscou, et al., "A Simple Cipher Governs DNA Recognition by TAL Effectors," Science, vol. 326, p. 1501 (2009).
Mui, et al., "Influence of Polyethylene Glycol Lipid Desorption Rates on Pharmacokinetics and Pharmacodynamics of siRNA Lipid Nanoparticles," Molecular Therapy, 2, 2013, e139.
Murauer, et al., "Functional Correction of Type VII Collagen Expression in Dystrophic Epidermolysis Bullosa," Journal of Investigative Dermatology, vol. 131, pp. 74-83, (2011).
Nabhan, et al., "Intrathecal delivery of frataxin mRNA encapsulated in lipid nanoparticles to dorsal root ganglia as a potential therapeutic for Friedreich's ataxia," Scientific Reports, 6, 2016.
Ng, et al., "A protocol describing the use of a recombinant protein-based, animal product-free medium (APEL) for human embryonic stem cell differentiation as spin embryoid bodies," Nat. Protoc. 3:768-776 (2008).
Niu, et al., "Engineering Variants of the I-SceI Homing Endonuclease with Strand-specific and Site-specific DNA-nicking Activity, Journal of Molecular Biology" vol. 382, pp. 188-202 (2008).
Niyomtham, et al., "Synthesis and in vitro transfection efficiency of spermine-based cationic lipids with different central core structures and lipophilic tails," Bioorganic & Medicianl Chemisty Letters, 25, 2015, pp. 496-503.
Okita, et al., "Generation of germline-competent induced pluripotent stem cells," Nature, vol. 448, pp. 313-317 (2007).
Osborn, et al., "Talen-based Gene Correction for Epidermolysis Bullosa," Molecular Therapy vol. 21, No. 6, pp. 1151-1159, (2013).
Ousterout, et al., Genetic Correction of Dystrophin by Engineered Nucleases, Mol. Ther., vol. 20, pp. S26-S27 (2012).
Pardi, et al., "Expression kinetics of nucleoside-modified mRNA delivered in lipid nanoparticles to mice by various routes," J Control Release, 217, Nov. 10, 2015, pp. 345-351.
Payton, et al., "Long Term Storage of Lyophilized Liposomal Formulations," Journal of Pharmaceutical Sciences, 103 (12), Dec. 2014, pp. 3869-3878.
Porteus, et al., "Gene targeting using zinc finger nucleases," Nat. Biotechnol., vol. 23, No. 8, pp. 967-973 (2005).
Potter, et al., "Transfection by Electroporation," Curr Protoc Mol Biol., Chapter: Unit-.3. doi:10.1002-0471142727.mb0903s62, pp. 1-12,(2003).
Remington, et al., "Injection of recombinant human type VII collagen corrects the disease phenotype in a murine model of dystrophic epidermolysis bullosa", Molecular Therapy. vol. 17, No. 1, pp. 26-33, (2009).
Rossi, et al., "Anti-inflammatory cyclopentenone prostaglandins are direct inhibitors of IκB kinase," Nature, vol. 403, pp. 103-108 (2000).
Sabnis, et al., "A Novel Amino Lipid Series for mRNA Delivery: Improved Endosomal Escape and Sustained Pharmacology and Safety in Non-human Primates," Molecular Therapy, vol. 26, No. 6, Jun. 2018, pp. 1509-1519.

Sander, et al., "Targeted gene disruption in somatic zebrafish cells using engineered TALENs," Author Manuscript, available in PMC on Feb. 5, 2012. Published in final edited form as: Nat Biotechnol; 29(8): 697-698 (2012).
Sanjana, et al., "A transcription activator-like effector toolbox for genome engineering," Nature Protocols, vol. 7, No. 1, pp. 171-192 (2012).
Schneider, "An Effective Method for Defatting Albumin Using Resin Columns," Biochim. Biophys. Acta, 221, 376-378, (1970).
Schwartz, et al., "Embryonic stem cell trials for macular degeneration: a preliminary report," Lancet. 379:713-720 (2012).
Sebastiano, et al. "In Situ Genetic Correction of the Sickle Cell Anemia Mutation in Human Induced Pluripotent Stem Cells Using Engineered Zinc Finger Nucleases" Stem Cells 29:1717-1726, (2011).
Semple, et al., "Rational design of cationic lipids for siRNA delivery," Nature Biotechnology, 28, 2010, pp. 172-176.
Shaker, et al., "Factors affecting liposomes particle size prepared by ethanol injection method," Res Pharma Sci, 12, 2017, pp. 347-352.
Shimizu, et al., "Transformation by Wnt Family Proteins Correlates with Regulation of β-Catenin," Cell Growth & Differentiation, vol. 8, pp. 1349-1358 (1997).
Shobaki, et al., "Mixing lipids to manipulate the ionization status of lipid nanoparticles for specific tissue targeting," International Journal of Nanomedicine, 13, 2013, pp. 8395-8410.
Soldner, et al., "Generation of isogenic pluripotent stem cells differing exclusively at two early onset Parkinson point mutations," Author Manuscript, available in PMC on Jul. 22, 2012. Published in final edited form as: Cell. Jul. 22, 2011; 146(2): 318-331 (2011).
Stark, et al., "Long-term stability of sterically stabilized liposomes by freezing and freeze-drying: Effects of cryoprotectans on structure," European Journal of Pharmaceutical Sciences, 41, 2010, pp. 546-555.
Su, et al. "CRISPR-Cas9 mediated efficient PD-1 disruption on human primary T cells from cancer patients." Sci. Rep. 6, 20070; doi: 10.1038/srep20070; pp. 1-13; Corrigendum, p. 1, (2016).
Sugii, et al., "Human and mouse adipose-derived cells support feeder-independent induction of pluripotent stem cells." PNAS, vol. 107, No. 8, pp. 2558-2563 (2010).
Sun and Zhao, "Seamless correction of the sickle cell disease mutation of the HBB gene in human induced pluripotent stem cells using TALENs" Biotechnology and Bioengineering 111(5):1048-1053 (2014).
Takahashi and Yamanaka, "Induction of pluripotent stem cells from mouse embryonic and adult fibroblast cultures by defined factors," Cell 126:663-676 (2006).
Takahashi, et al., "Induction of pluripotent stem cells from adult human fibroblasts by defined factors," Cell 131:861-872 (2007).
Teo, Pei Yun, "Nucleic acid delivery using poly(ethylenimine)-based polymers for programmed death-ligand 1 (PD-L1) knock-down in ovarian cancer to enhance immunotherapy," Ph.D. Dissertation, Imperial College, London, Jun. 2015.
Tesson, et al., "Knockout rats generated by embryo microinjection of TALENs," Nature Biotechnology, vol. 29, No. 8, pp. 695-696 (2011).
Titeux, et al., "Gene Therapy for Recessive Dystrophic Epidermolysis Bullosa," Dermatologic Clinics, vol. 28, pp. 361-366, (2010).
Tolar, et al., "Patient-Specific Naturally Gene-Reverted Induced Pluripotent Stem Cells in Recessive Dystrophic Epidermolysis Bullosa," Journal of Investigative Dermatology, vol. 134, pp. 1246-1254, (2014).
Wally, et al., "Spliceosome-Mediated Trans-Splicing: The Therapeutic Cut and Paste," Journal of Investigative Dermatology, vol. 132, pp. 1959-1966, (2012).
Warren, et al., "Highly efficient reprogramming to pluripotency and directed differentiation of human cells with synthetic modified mRNA," Cell. Stem Cell 7:618-630 (2010).
Watanabe, et al., "A Rock inhibitor permits survival of dissociated human embryonic stem cells," Nature Biotechnology, vol. 25, No. 6, pp. 681-686 (2007).
Wei, et al., "An Electroporation Chip Based on Flexible Microneedle Array for in Vivo Nucleic Acid Delivery," MEMS, 2014, San Francisco, CA, USA, pp. 817-820, (2014).

(56) References Cited

OTHER PUBLICATIONS

Wernig, et al., "In vitro reprogramming of fibroblasts into a pluripotent ES-cell-like state," Nature, vol. 448, pp. 317-324 (2007).
Whitehead, et al., "The in Vitro-in vivo Translation of Lipid Nanoparticles for Hepatocellular siRNA Delivery," ACS Nano, 6, 2012, pp. 6922-6929.
Wilson, et al., "Real Time Measurement of PEG Shedding from Lipid Nanoparticles in Serum via NMR Spectroscopy," Molecular Pharmaceutics, 12, 2015, pp. 386-392.
Wong, et al., "Potential of Fibroblast Cell Therapy for Recessive Dystrophic Epidermolysis Bullosa", Journal of Investigative Dermatology (2008) 128, 2179-2189.
Wood, et al., "Targeted Genome Editing Across Species Using ZFNs and TALENs," Science, vol. 333, p. 307 (2011).
Woodley, et al., "Intradermal injection of lentiviral vectors corrects regenerated human dystrophic epidermolysis bullosa skin tissue in vivo". Mol Ther; 10(2):318-26(2004).
Wu, et al., "TALEN-mediated genetic tailoring as a tool to analyze the function of acquired mutations in multiple myeloma cells," Blood Cancer Journal (2014), 4, e210, pp. 1-5.
"Xeno-Free System for hESC & hiPSC. Facilitating the Shift from Stem Cell Research to Clinical Applications." 12 pages, Biological Industries Catalog (Stem Cell Products) (2011).
Xie, et al., "Newly expressed proteins of mouse embryonic fibroblasts irradiated to be inactive," Biochem. Biophys. Res. Commun. 315, pp. 581-588 (2004).
Yakubov, et al., "Reprogramming of human fibroblasts to pluripotent stem cells using mRNA of four transcription factors," Biochem. Biophys. Res. Commun. 394:189-193 (2010).
Yanez, et al., "Successful reprogramming of cellular protein production through mRNA delivered by functionalized lipid nanoparticles," Proceedings of the National Academy of Sciences, 115, 2018, pp. E3350-E3360.
Yang, et al., "Overcoming the inhibitory effect of serum on lipofection by increasing the charge ratio of cationic liposome to DNA," Gene Therapy, 4, 1997, pp. 950-960.
Yang, et al., "Time-dependent maturation of cationic liposome-DNA complex for serum resistance," Gene Therapy, 5, 1998, pp. 380-387.
Yi, et al., "CRISPR-Cas9 therapeutics in cancer: promising strategies and present challenges," Biochimica et Biophysica Acta 1866, 2016, pp. 197-207.
You, et al., "Wnt signaling promotes oncogenic transformation by inhibiting c-Myc-induced apoptosis," The Journal of Cell Biology, vol. 157, No. 3, pp. 429-440 (2002).
Young, et al., "Background Mutations in Parental Cells Account for Most of the Genetic Heterogeneity of Induced Pluripotent Stem Cells," Cell Stem Cell 10, pp. 570-582 (2012).
Yu, et al., "Induced pluripotent stem cell lines derived from human somatic cells," Science 318:1917-1920 (2007).
Zhou, et al.," Generation of Induced Pluripotent Stem Cells Using Recombinant Proteins," Cell Stem Cell 4, pp. 1-4 (2009).

CATIONIC LIPIDS AND TRANSFECTION METHODS

PRIORITY

The present application is a continuation of U.S. application Ser. No. 16/526,621, filed Jul. 30, 2019, the content of which is hereby incorporated herein by reference in its entirety.

FIELD OF THE INVENTION

The present invention relates, in part, to various novel lipids, including methods, compositions, and products for delivering nucleic acids to cells.

BACKGROUND

Lipid-based materials, such as liposomes, are used as biological carriers for pharmaceutical and other biological applications, e.g., to introduce agents into cultured cell lines. Lipids are commonly used to deliver nucleic acids to cells in vitro under low-serum or serum-free conditions, for instance in transfection. However, serum components inhibit the activity of many lipids, limiting their use in the presence of serum, both in vitro and in vivo.

Improved lipid delivery systems, e.g., to achieve higher levels of transfection both in vitro and in vivo, are desirable. In particular, lipid delivery systems that are active in the presence of serum are needed. Improved levels of transfection will allow the treatment of disease states for which higher levels of expression than are currently achievable with lipid delivery systems are needed for therapeutic effect. Alternatively, higher transfection levels will allow for use of smaller amounts of material to achieve comparable expression levels, thereby decreasing potential toxicities and decreasing cost.

There is a need for novel lipids, lipid-like materials, and lipid-based delivery systems in the art.

SUMMARY OF THE INVENTION

Accordingly, the present invention relates to new lipids that find use, inter alia, in improved delivery of biological payloads, e.g. nucleic acids, to cells.

In aspects, the present invention relates to a compound of Formula (I)

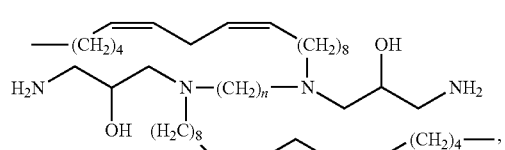

where n is 1, 2, 3, 4, 5, 6, 7, 8, 9, 10, 11, 12, 13, 14, or 15.

In embodiments, n is 1-12, or 2-12, or 1-10, or 2-10, or 1-8, or 2-8, or 2-6.

In embodiments, the present invention relates to compound (i):

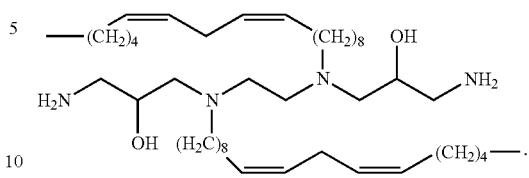

In embodiments, the present invention relates to compound (ii):

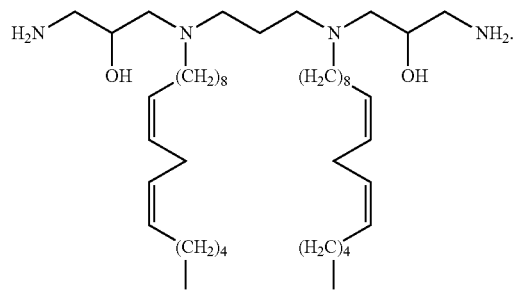

In embodiments, the present invention relates to compound (iii):

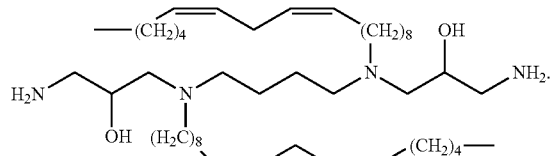

In embodiments, the present invention relates to compound (iv):

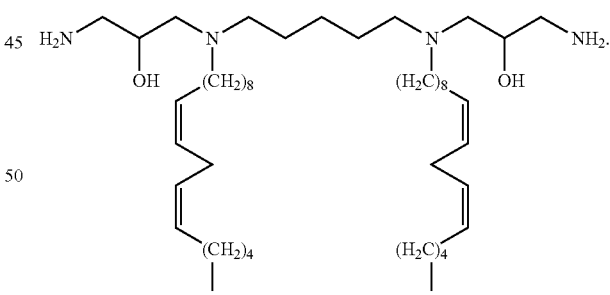

In embodiments, the present invention relates to compound (v):

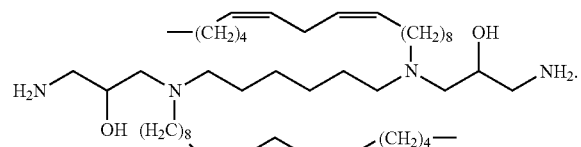

In embodiments, the present invention relates to compound (vi):

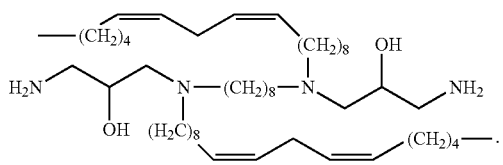

In embodiments, the present invention relates to compound (vii):

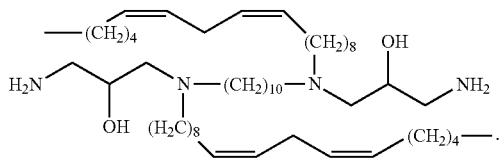

In embodiments, the present invention relates to compound (viii):

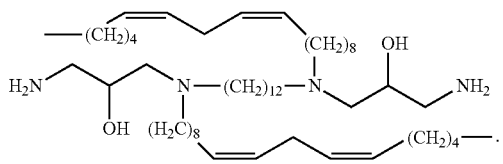

In embodiments, the present compounds (e.g. of Formula I) are components of a pharmaceutical composition and/or a lipid aggregate and/or a lipid carrier and/or a lipid nucleic-acid complex and/or a liposome and/or a lipid nanoparticle.

In embodiments, the present compounds (e.g. of Formula I) are components of a pharmaceutical composition and/or a lipid aggregate and/or a lipid carrier and/or a lipid nucleic-acid complex and/or a liposome and/or a lipid nanoparticle which does not require an additional or helper lipid.

In embodiments, the present compounds (e.g. of Formula I) are components of a pharmaceutical composition and/or a lipid aggregate and/or a lipid carrier and/or a lipid nucleic-acid complex and/or a liposome and/or a lipid nanoparticle which comprises a nucleic acid, such as DNA (e.g., without limitation, a plasmid, cosmid, phage, recombinant virus or other vector) or RNA (e.g., without limitation, an siRNA, micro-RNA (miRNA), long non-coding RNA (lncRNA), an in vitro transcribed RNA, a synthetic RNA, and/or an mRNA, in each case that comprises one or more non-canonical nucleotides that confer stability, avoid degradation by one or more nucleases, and/or avoid substantial cellular toxicity, or does not comprise a non-canonical nucleotide).

In aspects, the present invention relates to a method for transfecting a cell with a nucleic acid, comprising contacting the cell with a complex of the nucleic acid and a compound described herein (e.g. of Formula I), where the complex of the nucleic acid and the compound described herein (e.g. of Formula I) is optionally formed prior to contact with the cell.

In embodiments, the transfection method provides at least one of the following characteristics: (a) high transfection efficiency, (b) high level of endosomal escape, (c) serum-resistance, (d) low toxicity effects, (e) high level of protein expression, (f) transfectability in various cell types, and (g) transfectability without additional lipids or reagents for transfection, e.g. relative to a method of transfecting a cell with complex of the nucleic acid and DOTMA, DODMA, DOTAP, DODAP, DOPE, cholesterol, LIPOFECTIN (cationic liposome formulation), LIPOFECTAMINE (cationic liposome formulation), LIPOFECTAMINE 2000 (cationic liposome formulation), LIPOFECTAMINE 3000 (cationic liposome formulation), and combinations thereof.

The details of the invention are set forth in the accompanying description below. Although methods and materials similar or equivalent to those described herein can be used in the practice or testing of the present invention, illustrative methods and materials are now described. Other features, objects, and advantages of the invention will be apparent from the description and from the claims. In the specification and the appended claims, the singular forms also include the plural unless the context clearly dictates otherwise. Unless defined otherwise, all technical and scientific terms used herein have the same meaning as commonly understood by one of ordinary skill in the art to which this invention belongs.

Any aspect or embodiment disclosed herein can be combined with any other aspect or embodiment as disclosed herein.

DETAILED DESCRIPTION OF THE FIGURES

FIG. 1 depicts primary human epidermal keratinocytes cultured in a 24-well plate, and transfected with 400 ng per well of in vitro transcribed RNA encoding green fluorescent protein (GFP) complexed with the indicated lipid and with the indicated mass ratio of lipid to RNA. Complexation was performed in DMEM, and transfections were performed in 100% fetal bovine serum (FBS). Images were taken eight hours following transfection.

FIG. 2 depicts the experiment of FIG. 1, with fluorescence measured at the indicated time points following transfection using DHDLinS.

FIG. 3 depicts the results of an experiment conducted as in FIG. 1, but with the indicated amounts of RNA (in nanograms) and the indicated lipid-to-RNA mass ratios (in micrograms of lipid per microgram of RNA). Images were taken 16 hours following transfection. As shown in the figure, all RNA amounts and lipid-to-RNA mass ratios tested yielded a fluorescent signal.

DETAILED DESCRIPTION OF THE INVENTION

Figure 1:
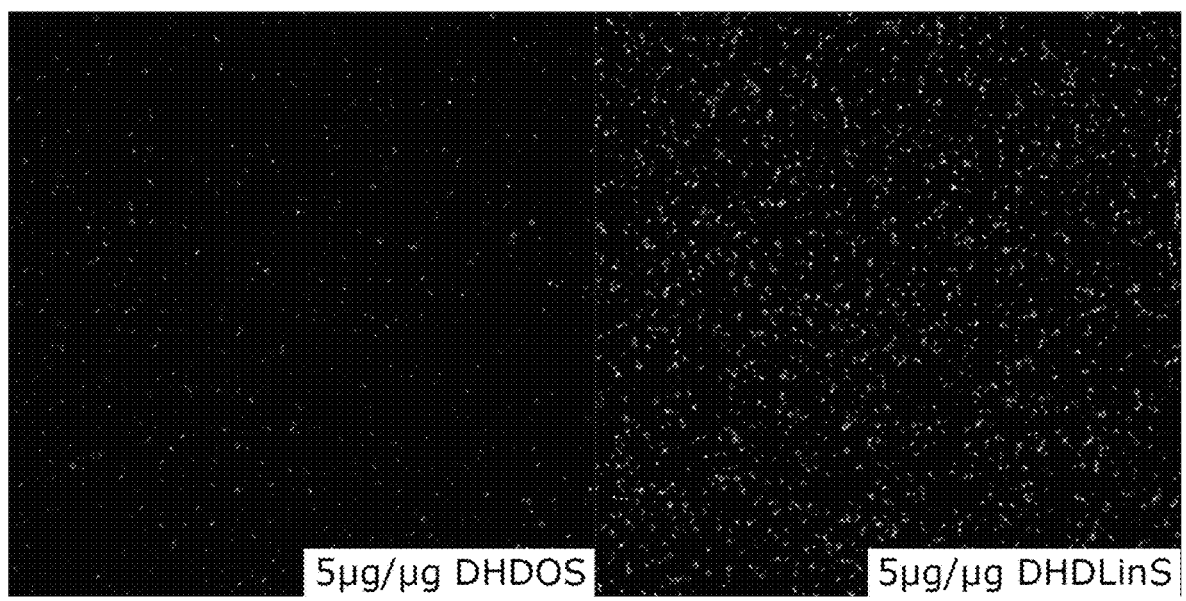

The present invention is based, in part, on the discovery of novel lipids that, inter alia, demonstrate superior abilities to support delivery of nucleic acids to cells, e.g. during transfection. The present invention provides such compositions, methods of making the compositions, and methods of using the compositions to introduce nucleic acids into cells, including for the treatment of diseases.

Compounds

In aspects, the present invention relates to a compound of Formula (I)

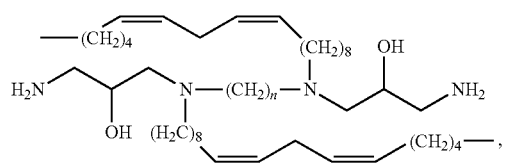

(I)

where n is 1, 2, 3, 4, 5, 6, 7, 8, 9, 10, 11, 12, 13, 14, or 15.

In embodiments, n is 1-14, or 1-12, or 1-10, or 1-8, or 1-6, or 1-4, or 1-2, or 2-14, or 2-12, or 2-10, or 2-8, or 2-6, or 2-4, or 4-14, or 4-12, or 4-10, or 4-8, or 4-6, or 6-14, or 6-12, or 6-10, or 6-8, or 8-14, or 8-12, or 8-10, or 10-14, or 10-12.

In embodiments, n is 1. In embodiments, n is 2. In embodiments, n is 3. In embodiments, n is 4. In embodiments, n is 5. In embodiments, n is 6. In embodiments, n is 7. In embodiments, n is 8. In embodiments, n is 9. In embodiments, n is 10. In embodiments, n is 11. In embodiments, n is 12. In embodiments, n is 13. In embodiments, n is 14. In embodiments, n is 15.

In embodiments, the present invention relates to compound (i):

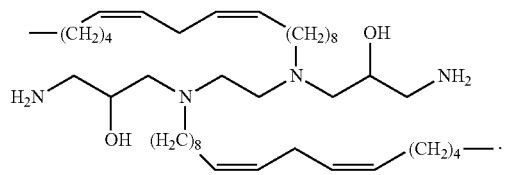

In embodiments, the present invention relates to compound (ii):

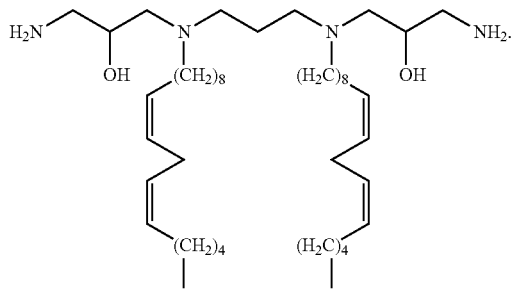

In embodiments, the present invention relates to compound (iii):

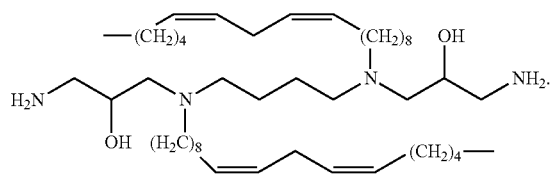

In embodiments, the present invention relates to compound (iv):

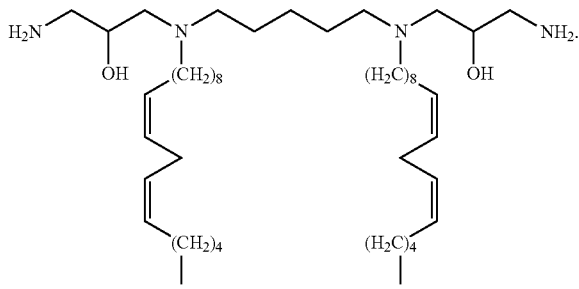

In embodiments, the present invention relates to compound (v):

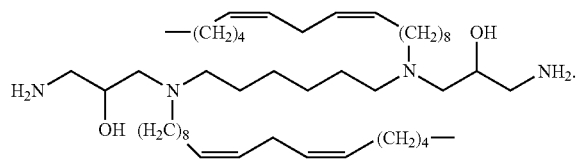

In embodiments, the present invention relates to compound (vi):

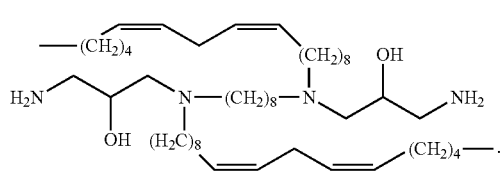

In embodiments, the present invention relates to compound (vii):

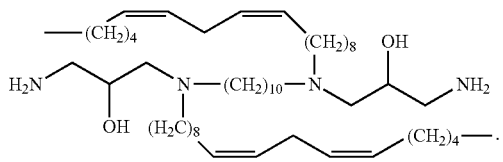

In embodiments, the present invention relates to compound (viii):

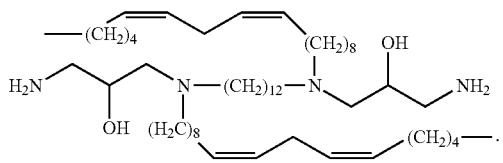

In embodiments, the present invention relates to a pharmaceutical composition and/or a lipid aggregate and/or a lipid carrier and/or a lipid nucleic-acid complex and/or a liposome and/or a lipid nanoparticle which comprises a compound described herein (e.g. of Formula I).

In embodiments, the pharmaceutical composition and/or lipid aggregate and/or lipid carrier and/or lipid nucleic-acid complex and/or liposome and/or lipid nanoparticle is in any physical form including, e. g., lipid nanoparticles, liposomes, micelles, interleaved bilayers, etc.

In embodiments, the pharmaceutical composition and/or lipid aggregate and/or lipid carrier is a liposome. In embodiments, the liposome is a large unilamellar vesicle (LUV), multilamellar vesicle (MLV) or small unilamellar vesicle (SUV). In embodiments, the liposome has a diameter up to about 50 to 80 nm. In embodiments, the liposome has a diameter of greater than about 80 to 1000 nm, or larger. In embodiments, the liposome has a diameter of about 50 to 1000 nm, e.g. about 200 nm or less. Size indicates the size (diameter) of the particles formed. Size distribution may be determined using quasi-elastic light scattering (QELS) on a Nicomp Model 370 sub-micron particle sizer.

In embodiments, the compound (e.g. of Formula I), and/or pharmaceutical composition and/or lipid aggregate and/or lipid carrier and/or lipid nucleic-acid complex and/or liposome and/or lipid nanoparticle comprising the compound (e.g. of Formula I), is soluble in an alcohol (e.g. ethyl alcohol) at room temperature (e.g. about 20-25° C.) and/or at low temperatures (e.g. about 000° C., or about −10° C., or about −20° C., or about −30° C., or about −40° C., or about −50° C., or about −60° C., or about −70° C., or about −80° C.).

In certain embodiments, the present invention relates to methods and compositions for producing lipid-encapsulated nucleic acid particles in which nucleic acids are encapsulated within a lipid layer. Such nucleic acid-lipid particles, including, without limitation incorporating RNAs, can be characterized using a variety of biophysical parameters including: drug to lipid ratio; encapsulation efficiency; and particle size. High drug to lipid ratios, high encapsulation efficiency, good nuclease resistance and serum stability and controllable particle size, generally less than 200 nm in diameter can, in certain situations, be desirable (without limitation).

Nucleic acid to lipid ratio can refer to the amount of nucleic acid in a defined volume of preparation divided by the amount of lipid in the same volume. This may be on a mole per mole basis, or on a weight per weight basis, or on a weight per mole basis, or on a mole per weight basis. For final, administration-ready formulations, the nucleic acid to lipid ratio may be calculated after dialysis, chromatography and/or enzyme (e.g., nuclease) digestion has been employed to remove as much external nucleic acid as possible.

Encapsulation efficiency can refer to the drug (including nucleic acid) to lipid ratio of the starting mixture divided by the drug (including nucleic acid) to lipid ratio of the final, administration competent formulation. This can be a measure of relative efficiency. For a measure of absolute efficiency, the total amount of nucleic acid added to the starting mixture that ends up in the administration competent formulation, can also be calculated. The amount of lipid lost during the formulation process may also be calculated. Efficiency can be used as a measure of the wastage and expense of the formulation.

In embodiments, the present compounds (e.g. of Formula I) and/or pharmaceutical compositions and/or lipid aggregates and/or lipid carriers and/or lipid nucleic-acid complexes and/or liposomes and/or lipid nanoparticles have utility for delivery of macromolecules and other compounds into cells. In embodiments, the present compounds (e.g. of Formula I) and/or pharmaceutical compositions and/or lipid aggregates and/or lipid carriers and/or lipid nucleic-acid complexes and/or liposomes and/or lipid nanoparticles have utility for delivery of nucleic acids into cells.

In embodiments, there is provided a method for transfecting a cell with a nucleic acid, comprising contacting the cell with a complex of the nucleic acid and a present compound (e.g. of Formula I) and/or pharmaceutical composition and/or lipid aggregate and/or lipid carrier and/or lipid nucleic-acid complex and/or liposome and/or lipid nanoparticle. In embodiments, the complex of the nucleic acid and the present compound (e.g. of Formula I) and/or pharmaceutical composition and/or lipid aggregate and/or lipid carrier and/or lipid nucleic-acid complex and/or liposome and/or lipid nanoparticle is formed prior to contact with the cell.

In embodiments, the present compounds (e.g. of Formula I) and/or pharmaceutical compositions and/or lipid aggregates and/or lipid carriers and/or lipid nucleic-acid complexes and/or liposomes and/or lipid nanoparticles encapsulate nucleic acids with high-efficiency, and/or have high drug to lipid ratios, and/or protect the encapsulated nucleic acid from degradation and/or clearance in serum, and/or are suitable for systemic delivery, and/or provide intracellular delivery of the encapsulated nucleic acid. In addition, in embodiments, the present compounds (e.g. of Formula I) and/or pharmaceutical compositions and/or lipid aggregates and/or lipid carriers and/or lipid nucleic-acid complexes and/or liposomes and/or lipid nanoparticles are well-tolerated and provide an adequate therapeutic index, such that patient treatment at an effective dose of the nucleic acid is not associated with significant toxicity and/or unacceptable risk to the patient.

In embodiments, the present compounds (e.g. of Formula I) and/or pharmaceutical compositions and/or lipid aggregates and/or lipid carriers and/or lipid nucleic-acid complexes and/or liposomes and/or lipid nanoparticles are polycationic. In embodiments, the present compounds (e.g. of Formula I) and/or pharmaceutical compositions and/or lipid aggregates and/or lipid carriers and/or lipid nucleic-acid complexes and/or liposomes and/or lipid nanoparticles form stable complexes with various anionic macromolecules, such as polyanions, such as nucleic acids, such as RNA or DNA. In embodiments, the present compounds (e.g. of Formula I) and/or pharmaceutical compositions and/or lipid aggregates and/or lipid carriers and/or lipid nucleic-acid complexes and/or liposomes and/or lipid nanoparticles, have the property, when dispersed in water, of forming lipid aggregates which strongly, via their cationic portion, associate with polyanions. In embodiments, by modulating the amount of cationic charges relative to the anionic compound, for example by using an excess of cationic charges relative to the anionic compound, the polyanion-lipid complexes may be adsorbed on cell membranes, thereby facilitating uptake of the desired compound by the cells.

In embodiments, the present compounds (e.g. of Formula I) and/or pharmaceutical compositions and/or lipid aggregates and/or lipid carriers and/or lipid nucleic-acid complexes and/or liposomes and/or lipid nanoparticles mediate one or more of (i) compacting a nucleic acid payload to be delivered, which may protect it from nuclease degradation and/or may enhance receptor-mediated uptake, (ii) improving association with negatively-charged cellular membranes, which may be modulated by giving the complexes a positive charge, (iii) promoting fusion with endosomal membranes, which may facilitate the release of complexes from endosomal compartments, and (iv) enhancing transport from the cytoplasm to the nucleus.

In embodiments, the present invention relates to the present compounds (e.g. of Formula I) and/or pharmaceutical compositions and/or lipid aggregates and/or lipid carriers and/or lipid nucleic-acid complexes and/or liposomes and/or lipid nanoparticles for transfection, or methods of transfection, which have a high transfection efficiency. In embodiments, the transfection efficiency is measured by assaying a percentage of cells that are transfected compared to the entire population, during a transfection protocol. In various embodiments, the transfection efficiency of the present compositions and methods is greater than about 30%, or greater than about 40%, or greater than about 50%, or greater than about 60%, or greater than about 70%, or greater than about 80%, or greater than about 90%, or greater than about 95%. In various embodiments, the transfection efficiency of the present compositions and methods is greater than the transfection efficiency of commercially available products (e.g. LIPOFECTIN (cationic liposome formulation), LIPOFECTAMINE (cationic liposome formulation), LIPOFECTAMINE 2000 (cationic liposome formulation), LIPOFECTAMINE 3000 (cationic liposome formulation) (Life Technologies)). In various embodiments, the transfection efficiency of the present compositions and methods is about 1.1-fold, or about 1.5-fold, or about 2-fold, or about 5-fold, or about 10-fold, or about 15-fold, or about 20-fold, or about 30-fold, or about 50-fold, or greater than about 50-fold greater than the transfection efficiency of commercially available products (e.g. LIPOFECTIN (cationic liposome formulation), LIPOFECTAMINE (cationic liposome formulation), LIPOFECTAMINE 2000 (cationic liposome formulation), LIPOFECTAMINE 3000 (cationic liposome formulation) (Life Technologies)).

In embodiments, the present invention relates to the present compounds (e.g. of Formula I) and/or pharmaceutical compositions and/or lipid aggregates and/or lipid carriers for transfection, or methods of transfection, which permit a high level of endosomal escape. In various embodiments, the endosomal escape of the present compositions and methods is greater than the endosomal escape of commercially available products (e.g. LIPOFECTIN (cationic liposome formulation), LIPOFECTAMINE (cationic liposome formulation), LIPOFECTAMINE 2000 (cationic liposome formulation), LIPOFECTAMINE 3000 (cationic liposome formulation) (Life Technologies)). In various embodiments, the endosomal escape of the present compositions and methods is about 5-fold, or 10-fold, or 15-fold, or 20-fold, or 30-fold greater than the endosomal escape of commercially available products (e.g. LIPOFECTIN (cationic liposome formulation), LIPOFECTAMINE (cationic liposome formulation), LIPOFECTAMINE 2000 (cationic liposome formulation), LIPOFECTAMINE 3000 (cationic liposome formulation) (Life Technologies)).

In embodiments, the present compounds (e.g. of Formula I) and/or pharmaceutical compositions and/or lipid aggregates and/or lipid carriers and/or lipid nucleic-acid complexes and/or liposomes and/or lipid nanoparticles are serum-resistant. In embodiments, the present compounds (e.g. of Formula I) and/or pharmaceutical compositions and/or lipid aggregates and/or lipid carriers and/or lipid nucleic-acid complexes and/or liposomes and/or lipid nanoparticles are substantially stable in serum. In embodiments, the present transfection methods can function in the presence of serum and/or do not require serum inactivation and/or media changes. In embodiments, the stability in serum and/or serum-resistance is measurable via in vitro assays known in the art. Transfection efficiency in varying amounts of serum may be used to assess the ability to transfect a macromolecule (e.g., without limitation, DNA or RNA), optionally in comparison to commercially available products (e.g. LIPOFECTIN (cationic liposome formulation), LIPOFECTAMINE (cationic liposome formulation), LIPOFECTAMINE 2000 (cationic liposome formulation), LIPOFECTAMINE 3000 (cationic liposome formulation) (Life Technologies)).

In embodiments, the present compounds (e.g. of Formula I) and/or pharmaceutical compositions and/or lipid aggregates and/or lipid carriers and/or lipid nucleic-acid complexes and/or liposomes and/or lipid nanoparticles for transfection, or methods of transfection, have low or reduced toxicity effects. In embodiments, the present compounds (e.g. of Formula I) and/or pharmaceutical compositions and/or lipid aggregates and/or lipid carriers and/or lipid nucleic-acid complexes and/or liposomes and/or lipid nanoparticles for transfection, or methods of transfection, have reduced toxicity effects as compared to commercially available products (e.g. LIPOFECTIN (cationic liposome formulation), LIPOFECTAMINE (cationic liposome formulation), LIPOFECTAMINE 2000 (cationic liposome formulation), LIPOFECTAMINE 3000 (cationic liposome formulation) (Life Technologies)). In various embodiments, the present compositions and methods allow for cells having greater than about 50%, or about 60%, or about 70%, or about 80%, or about 90%, or about 95% viability after transfection. In various embodiments, the present compositions and methods allow for cells having about 1.1-fold, or about 1.5-fold, or about 2-fold, or about 5-fold, or about 10-fold, or about 15-fold, or about 20-fold, or about 30-fold greater viability after transfection, as compared to commercially available products (e.g. LIPOFECTIN (cationic liposome formulation), LIPOFECTAMINE (cationic liposome formulation), LIPOFECTAMINE 2000 (cationic liposome formulation), LIPOFECTAMINE 3000 (cationic liposome formulation) (Life Technologies)). In embodiments, toxicity effects include disruption of cell morphology and/or viability or deregulation of one or more genes.

In embodiments, the present compounds (e.g. of Formula I) and/or pharmaceutical compositions and/or lipid aggregates and/or lipid carriers and/or lipid nucleic-acid complexes and/or liposomes and/or lipid nanoparticles for transfection, or methods of transfection, permit a high level of protein expression from the nucleic acid (e.g. DNA or RNA) being transfected. In various embodiments, the protein expression of the present compositions and methods is greater than about 30%, or greater than about 40%, or greater than about 50%, or greater than about 60%, or greater than about 70%, or greater than about 80%, or greater than about 90%, or greater than about 95% more than in un-transfected cells and/or cells contacted with naked nucleic acid. In various embodiments, the resultant protein expression of the present compositions and methods is greater than the resultant protein expression of commercially available products (e.g. LIPOFECTIN (cationic liposome formulation), LIPOFECTAMINE (cationic liposome formulation), LIPOFECTAMINE 2000 (cationic liposome formulation), LIPOFECTAMINE 3000 (cationic liposome formulation) (Life Technologies)). In various embodiments, the resultant protein expression of the present compositions and methods is about 1.1-fold, or about 1.5-fold, or about 2-fold, or about 5-fold, or about 10-fold, or about 15-fold, or about 20-fold, or about 30-fold, or about 50-fold, or greater than about 50-fold greater than the resultant protein expression of commercially available products (e.g. LIPOFECTIN (cationic liposome formulation), LIPOFECTAMINE (cationic liposome formulation), LIPOFECTAMINE 2000 (cationic liposome formulation), LIPOFECTAMINE 3000 (cationic liposome formulation) (Life Technologies)).

In embodiments, the present invention relates to the present compounds (e.g. of Formula I) and/or pharmaceutical compositions and/or lipid aggregates and/or lipid carriers and/or lipid nucleic-acid complexes and/or liposomes and/or lipid nanoparticles for transfection, or methods of transfection, which allow for transfection, including efficient transfection as described herein, in various cell types. In embodiments, the present compounds (e.g. of Formula I) and/or pharmaceutical compositions and/or lipid aggregates and/or lipid carriers for transfection, or methods of transfection, allow for transfection, including efficient transfection as described herein, in established cell lines, hard-to-transfect cells, primary cells, stem cells, and blood cells. In embodiments, the cell type is a keratinocyte, a fibroblast, a PBMC, or a dendritic cell.

In embodiments, a present compound (e.g. of Formula I), pharmaceutical composition and/or a lipid aggregate and/or a lipid carrier and/or lipid nucleic-acid complex and/or liposome and/or lipid nanoparticle is suitable for transfection or delivery of compounds to target cells, either in vitro or in vivo.

In embodiments, the present compounds (e.g. of Formula I) and/or pharmaceutical compositions and/or lipid aggregates and/or lipid carriers and/or lipid nucleic-acid complexes and/or liposomes and/or lipid nanoparticles for transfection, or methods of transfection, do not require additional reagents for transfection, e.g. PLUS™ Reagent (DNA pre-complexation reagent) (Life Technologies).

In embodiments, the present compounds (e.g. of Formula I) are components of a pharmaceutical composition and/or a lipid aggregate and/or a lipid carrier and/or lipid nucleic-acid complex and/or liposome and/or lipid nanoparticle which does not require an additional or helper lipid, e.g. for efficient transfection. In embodiments, the pharmaceutical composition and/or a lipid aggregate and/or a lipid carrier and/or lipid nucleic-acid complex and/or liposome and/or lipid nanoparticle does not require one or more of: DOPE, DOPC, cholesterol, and a polyethylene glycol (PEG)-modified lipid (inclusive, without limitation, of a PEGylated PE phospholipid, PC phospholipid, and/or cholesterol), e.g. for efficient transfection.

In embodiments, the present compounds (e.g. of Formula I) are components of a pharmaceutical composition and/or a lipid aggregate and/or a lipid carrier and/or lipid nucleic-acid complex and/or liposome and/or lipid nanoparticle that further comprises an additional or helper lipid.

In embodiments, the additional or helper lipid is selected from one or more of the following categories: cationic lipids; anionic lipids; neutral lipids; multi-valent charged lipids; and zwitterionic lipids. In some embodiments, a cationic lipid may be used to facilitate a charge-charge interaction with nucleic acids.

In embodiments, the additional or helper lipid is a neutral lipid. In embodiments, the neutral lipid is dioleoylphosphatidylethanolamine (DOPE), 1,2-Dioleoyl-sn-glycero-3-phosphocholine (DOPC), or cholesterol. In embodiments, cholesterol is derived from plant sources. In other embodiments, cholesterol is derived from animal, fungal, bacterial or archaeal sources.

In embodiments, the additional or helper lipid is a cationic lipid. In embodiments, the cationic lipid is N-[1-(2,3-dioleoyloxy)propyl]-N,N,N-trimethylammonium chloride (DOTMA), 1,2-bis(oleoyloxy)-3-3-(trimethylammonia) propane (DOTAP), or 1,2-dioleoyl-3-dimethylammonium-propane (DODAP).

In embodiments, one or more of the phospholipids 18:0 PC, 18:1 PC, 18:2 PC, DMPC, DSPE, DOPE, 18:2 PE, DMPE, or a combination thereof are used as helper lipids. In embodiments, the additional or helper lipid is DOTMA and DOPE, optionally in a ratio of about 1:1. In embodiments, the additional or helper lipid is DHDOS and DOPE, optionally in a ratio of about 1:1.

In embodiments, the additional or helper lipid is a commercially available product (e.g. LIPOFECTIN (cationic liposome formulation), LIPOFECTAMINE (cationic liposome formulation), LIPOFECTAMINE 2000 (cationic liposome formulation), LIPOFECTAMINE 3000 (cationic liposome formulation) (Life Technologies)).

In embodiments, the additional or helper lipid is a compound having the Formula (A):

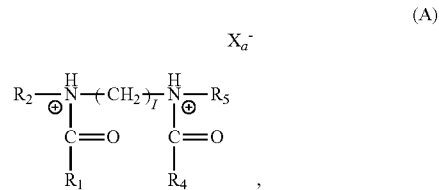

where, R1 and R4 are straight-chain alkenyl having 17 carbon atoms; R2 and R5 are —(CH2)p-NH2 where p is 1-4; l is 1-10; and Xa is a physiologically acceptable anion.

In one embodiment, the present compounds (e.g. of Formula I) and/or pharmaceutical compositions and/or lipid aggregates and/or lipid carriers and/or lipid nucleic-acid complexes and/or liposomes and/or lipid nanoparticles include one or more polyethylene glycol (PEG) chains, optionally selected from PEG200, PEG300, PEG400, PEG600, PEG800, PEG1000, PEG1500, PEG2000, PEG3000, and PEG4000. In embodiments, the PEG is PEG2000. In embodiments, the present compounds (e.g. of Formula I) and/or pharmaceutical compositions and/or lipid aggregates and/or lipid carriers and/or lipid nucleic-acid complexes and/or liposomes and/or lipid nanoparticles include 1,2-distearoyl-sn-glycero-3-phosphoethanolamine (DSPE) or a derivative thereof. In one embodiment, the present compounds (e.g. of Formula I) and/or pharmaceutical compositions and/or lipid aggregates and/or lipid carriers and/or lipid nucleic-acid complexes and/or liposomes and/or lipid nanoparticles comprise 1,2-distearoyl-sn-glycero-3-phosphoethanolamine-N-[methoxy(polyethylene glycol)-2000] (DSPE-PEG); in another embodiment, the present compounds (e.g. of Formula I) and/or pharmaceutical compositions and/or lipid aggregates and/or lipid carriers and/or lipid nucleic-acid complexes and/or liposomes and/or lipid nanoparticles comprise 1,2-dimyristoyl-sn-glycero-3-phosphoethanolamine-N-[methoxy(polyethylene glycol)-2000] (DMPE-PEG); in yet another embodiment, the present compounds (e.g. of Formula I) and/or pharmaceutical compositions and/or lipid aggregates and/or lipid carriers and/or lipid nucleic-acid complexes and/or liposomes and/or lipid nanoparticles comprise 1,2-dimyristoyl-rac-glycero-3-methoxypolyethylene glycol-2000 (DMG-PEG). In further embodiments, the present compounds (e.g. of Formula I) and/or pharmaceutical compositions and/or lipid aggregates and/or lipid carriers and/or lipid nucleic-acid complexes and/or liposomes and/or lipid nanoparticles comprise a mixture of PEGylated lipids and/or free PEG chains.

In embodiments, the present compounds (e.g. of Formula I) and/or pharmaceutical compositions and/or lipid aggregates and/or lipid carriers and/or lipid nucleic-acid complexes and/or liposomes and/or lipid nanoparticles comprise one or more of N-(carbonyl-ethoxypolyethylene glycol 2000)-1,2-distearoyl-sn-glycero-3-phosphoethanolamine (MPEG2000-DSPE), fully hydrogenated phosphatidylcholine, cholesterol, LIPOFECTAMINE 2000 (cationic liposome formulation), LIPOFECTAMINE 3000 (cationic liposome formulation), a cationic lipid, a polycationic lipid, and 1,2-distearoyl-sn-glycero-3-phosphoethanolamine-N-[folate(polyethylene glycol)-5000] (FA-M PEG5000-DSPE).

In one embodiment, the present compounds (e.g. of Formula I) and/or pharmaceutical compositions and/or lipid aggregates and/or lipid carriers and/or lipid nucleic-acid complexes and/or liposomes and/or lipid nanoparticles comprise about 3.2 mg/mL N-(carbonyl-ethoxypolyethylene glycol 2000)-1,2-distearoyl-sn-glycero-3-phosphoethanolamine (MPEG2000-DSPE), about 9.6 mg/mL fully hydrogenated phosphatidylcholine, about 3.2 mg/mL cholesterol, about 2 mg/mL ammonium sulfate, and histidine as a buffer, with about 0.27 mg/mL 1,2-distearoyl-sn-glycero-3-phosphoethanolamine-N-[folate(polyethylene glycol)-5000] (FA-MPEG5000-DSPE). In another embodiment, the nucleic acids are complexed by combining 1 μL of LIPOFECTAMINE 3000 (cationic liposome formulation) per about 1 μg of nucleic acid and incubating at room temperature for at least about 5 minutes. In one embodiment, the LIPOFECTAMINE 3000 (cationic liposome formulation) is a solution comprising a lipid at a concentration of about 1 mg/mL. In embodiments, nucleic acids are encapsulated by combining about 1 μg, or about 2 μg, or about 5 μg, or about 10 μg of the present compounds (e.g. of Formula I) and/or pharmaceutical compositions and/or lipid aggregates and/or lipid carriers and/or lipid nucleic-acid complexes and/or liposomes and/or lipid nanoparticles per about 1 μg of nucleic acid and incubating at room temperature for about 5 minutes or longer than about 5 minutes.

In embodiments, the present compounds (e.g. of Formula I) and/or pharmaceutical compositions and/or lipid aggregates and/or lipid carriers and/or lipid nucleic-acid complexes and/or liposomes and/or lipid nanoparticles comprise one or more nanoparticles. In one embodiment, the nanoparticle is a polymeric nanoparticle. In various embodiments, the present compounds (e.g. of Formula I) and/or pharmaceutical compositions and/or lipid aggregates and/or lipid carriers and/or lipid nucleic-acid complexes and/or liposomes and/or lipid nanoparticles comprise one or more of a diblock copolymer, a triblock copolymer, a tetrablock copolymer, and a multiblock copolymer. In various embodiments, the present compounds (e.g. of Formula I) and/or pharmaceutical compositions and/or lipid aggregates and/or lipid carriers and/or lipid nucleic-acid complexes and/or liposomes and/or lipid nanoparticles comprise one or more of polymeric nanoparticles comprising a polyethylene glycol (PEG)-modified polylactic acid (PLA) diblock copolymer (PLA-PEG), PEG-polypropylene glycol-PEG-modified PLA-tetrablock copolymer (PLA-PEG-PPG-PEG), and Poly (lactic-co-glycolic acid) copolymer. In another embodiment, the present compounds (e.g. of Formula I) and/or pharmaceutical compositions and/or lipid aggregates and/or lipid carriers and/or lipid nucleic-acid complexes and/or liposomes and/or lipid nanoparticles comprise a statistical, or an alternating, or a periodic copolymer, or any other sort of polymer.

In embodiments, the present compounds (e.g. of Formula I) and/or pharmaceutical compositions and/or lipid aggregates and/or lipid carriers and/or lipid nucleic-acid complexes and/or liposomes and/or lipid nanoparticles comprise one or more lipids that are described in WO/2000/027795, the entire contents of which are hereby incorporated herein by reference.

In embodiments, the present compounds (e.g. of Formula I) and/or pharmaceutical compositions and/or lipid aggregates and/or lipid carriers and/or lipid nucleic-acid complexes and/or liposomes and/or lipid nanoparticles comprises Polybrene™ (hexadimethrine bromide) as described in U.S. Pat. No. 5,627,159, the entire contents of which are incorporated herein by reference.

In various embodiments, the present compounds (e.g. of Formula I) and/or pharmaceutical compositions and/or lipid aggregates and/or lipid carriers and/or lipid nucleic-acid complexes and/or liposomes and/or lipid nanoparticles comprise one or more polymers. Examples of polymer include hexadimethrine bromide (Polybrene™), DEAE-Dextran, protamine, protamine sulfate, poly-L-lysine, or poly-D-lysine. These polymers may be used in combination with cationic lipids to result in synergistic effects on uptake by cells, stability of the present compounds (e.g. of Formula I) and/or pharmaceutical compositions and/or lipid aggregates and/or lipid carriers and/or lipid nucleic-acid complexes and/or liposomes and/or lipid nanoparticles, including serum stability (e.g., stability in vivo), endosomal escape, cell viability, and protein expression.

In embodiments, the present compounds (e.g. of Formula I) and/or pharmaceutical compositions and/or lipid aggregates and/or lipid carriers and/or lipid nucleic-acid complexes and/or liposomes and/or lipid nanoparticles are suitable for associating with a nucleic acid, inclusive of, for instance, include any oligonucleotide or polynucleotide.

In embodiments, nucleic acids are fully encapsulated within the present compounds (e.g. of Formula I) and/or pharmaceutical compositions and/or lipid aggregates and/or lipid carriers and/or lipid nucleic-acid complexes and/or liposomes and/or lipid nanoparticles. In other embodiments, nucleic acids are partially encapsulated within the present compounds (e.g. of Formula I) and/or pharmaceutical compositions and/or lipid aggregates and/or lipid carriers and/or lipid nucleic-acid complexes and/or liposomes and/or lipid nanoparticles. In still other embodiments, nucleic acids and the present compounds (e.g. of Formula I) and/or pharmaceutical compositions and/or lipid aggregates and/or lipid carriers and/or lipid nucleic-acid complexes and/or liposomes and/or lipid nanoparticles are both present with no encapsulation of the nucleic acids within the present compounds (e.g. of Formula I) and/or pharmaceutical compositions and/or lipid aggregates and/or lipid carriers and/or lipid nucleic-acid complexes and/or liposomes and/or lipid nanoparticles.

Fully encapsulated can indicate that the nucleic acid in the present compounds (e.g. of Formula I) and/or pharmaceutical compositions and/or lipid aggregates and/or lipid carriers and/or lipid nucleic-acid complexes and/or liposomes and/or lipid nanoparticles is not significantly degraded after exposure to serum or a nuclease assay that would significantly degrade free nucleic acids. In embodiments, less than about 25% of particle nucleic acid is degraded in a treatment that would normally degrade about 100% of free nucleic acid. In embodiments, less than about 10% or less than about 5% of the particle nucleic acid is degraded.

Extent of encapsulation may be determined by an Oligreen assay. Oligreen is an ultra-sensitive fluorescent nucleic acid stain for quantitating oligonucleotides and single-stranded DNA in solution (available from Invitrogen Corporation, Carlsbad, Calif.).

In embodiments, the present compounds (e.g. of Formula I) and/or pharmaceutical compositions and/or lipid aggregates and/or lipid carriers and/or lipid nucleic-acid complexes and/or liposomes and/or lipid nanoparticles are serum stable and/or they do not rapidly decompose into their component parts upon in vivo administration.

In embodiments, the present compounds (e.g. of Formula I) and/or pharmaceutical compositions and/or lipid aggregates and/or lipid carriers and/or lipid nucleic-acid complexes and/or liposomes and/or lipid nanoparticles are complexed with a nucleic acid (e.g. DNA or RNA) in a ratio, which may depend on the target cell type, generally ranging from about 1:16 to about 25:1 ng lipid:ng DNA or RNA. Illustrative lipid:DNA or RNA ratios are from about 1:1 to about 10:1, e.g. about 1:1, or about 2:1, or about 3:1, or about 4:1 or about 5:1, or about 6:1, or about 7:1, or about 8:1, or about 9:1, or about 10:1.

In embodiments, additional parameters such as nucleic acid concentration, buffer type and concentration, etc., are selected to achieve a desired transfection efficiency, e.g., high transfection efficiency.

In embodiments, the nucleic acid is selected from RNA or DNA.

In embodiments, the DNA is a plasmid, cosmid, phage, recombinant virus or other vector. In embodiments, a vector (or plasmid) refers to discrete elements that are used to, for example, introduce heterologous nucleic acid into cells for expression or replication thereof. In embodiments, the vectors can remain episomal or can be designed to effect integration of a gene or portion thereof into a chromosome of the genome. Also contemplated are vectors that are artificial chromosomes, such as yeast artificial chromosomes and mammalian artificial chromosomes. Included, without limitation, are vectors capable of expressing DNA that is operatively linked with regulatory sequences, such as promoter regions, that are capable of effecting expression of such DNA fragments (e.g. expression vectors). Thus, a vector can refer to a recombinant DNA or RNA construct, such as a plasmid, a phage, recombinant virus or other vector that, upon introduction into an appropriate host cell, results in expression of the DNA. Appropriate vectors can include, without limitation, those that are replicable in eukaryotic cells and/or prokaryotic cells and those that remain episomal or those that integrate into the host cell genome.

In embodiments, the nucleic acid is an RNA, messenger RNA (mRNA), a small interfering RNA (siRNA), micro RNA (miRNA), long non-coding RNA (lncRNA), antisense oligonucleotide, ribozyme, plasmid, immune stimulating nucleic acid, antisense, antagomir, antimir, microRNA mimic, supermir, U1 adaptor, or aptamer.

In embodiments, the RNA is a synthetic RNA. In embodiments, the RNA is a chemically synthesized RNA. In embodiments, the RNA is an in vitro transcribed RNA.

In embodiments, the synthetic RNA (inclusive, without limitation, of mRNA) does not comprise a non-canonical nucleotide. In embodiments, the synthetic RNA (inclusive, without limitation of mRNA) comprises one or more non-canonical nucleotides. In embodiments, the one or more non-canonical nucleotides is selected from 2-thiouridine, 5-azauridine, pseudouridine, 4-thiouridine, 5-methyluridine, 5-methylpseudouridine, 5-aminouridine, 5-aminopseudouridine, 5-hydroxyuridine, 5-hydroxypseudouridine, 5-methoxyuridine, 5-methoxypseudouridine, 5-ethoxyuridine, 5-ethoxypseudouridine, 5-hydroxymethyluridine, 5-hydroxymethylpseudouridine, 5-carboxyuridine, 5-carboxypseudouridine, 5-formyluridine, 5-formylpseudouridine, 5-methyl-5-azauridine, 5-amino-5-azauridine, 5-hydroxy-5-azauridine, 5-methylpseudouridine, 5-aminopseudouridine, 5-hydroxypseudouridine, 4-thio-5-azauridine, 4-thiopseudouridine, 4-thio-5-methyluridine, 4-thio-5-aminouridine, 4-thio-5-hydroxyuridine, 4-thio-5-methyl-5-azauridine, 4-thio-5-amino-5-azauridine, 4-thio-5-hydroxy-5-azauridine, 4-thio-5-methylpseudouridine, 4-thio-5-aminopseudouridine, 4-thio-5-hydroxypseudouridine, 2-thiocytidine, 5-azacytidine, pseudoisocytidine, N4-methylcytidine, N4-aminocytidine, N4-hydroxycytidine, 5-methylcytidine, 5-aminocytidine, 5-hydroxycytidine, 5-methoxycytidine, 5-ethoxycytidine, 5-hydroxymethylcytidine, 5-carboxycytidine, 5-formylcytidine, 5-methyl-5-azacytidine, 5-amino-5-azacytidine, 5-hydroxy-5-azacytidine, 5-methylpseudoisocytidine, 5-aminopseudoisocytidine, 5-hydroxypseudoisocytidine, N4-methyl-5-azacytidine, N4-methylpseudoisocytidine, 2-thio-5-azacytidine, 2-thiopseudoisocytidine, 2-thio-N4-methylcytidine, 2-thio-N4-aminocytidine, 2-thio-N4-hydroxycytidine, 2-thio-5-methylcytidine, 2-thio-5-aminocytidine, 2-thio-5-hydroxycytidine, 2-thio-5-methyl-5-azacytidine, 2-thio-5-amino-5-azacytidine, 2-thio-5-hydroxy-5-azacytidine, 2-thio-5-methylpseudoisocytidine, 2-thio-5-aminopseudoisocytidine, 2-thio-5-hydroxypseudoisocytidine, 2-thio-N4-methyl-5-azacytidine, 2-thio-N4-methylpseudoisocytidine, N4-methyl-5-methylcytidine, N4-methyl-5-aminocytidine, N4-methyl-5-hydroxycytidine, N4-methyl-5-methyl-5-azacytidine, N4-methyl-5-amino-5-azacytidine, N4-methyl-5-hydroxy-5-azacytidine, N4-methyl-5-methylpseudoisocytidine, N4-methyl-5-aminopseudoisocytidine, N4-methyl-5-hydroxypseudoisocytidine, N4-amino-5-azacytidine, N4-aminopseudoisocytidine, N4-amino-5-methylcytidine, N4-amino-5-aminocytidine, N4-amino-5-hydroxycytidine, N4-amino-5-methyl-5-azacytidine, N4-amino-5-amino-5-azacytidine, N4-amino-5-hydroxy-5-azacytidine, N4-amino-5-methylpseudoisocytidine, N4-amino-5-aminopseudoisocytidine, N4-amino-5-hydroxypseudoisocytidine, N4-hydroxy-5-azacytidine, N4-hydroxypseudoisocytidine, N4-hydroxy-5-methylcytidine, N4-hydroxy-5-aminocytidine, N4-hydroxy-5-hydroxycytidine, N4-hydroxy-5-methyl-5-azacytidine, N4-hydroxy-5-amino-5-azacytidine, N4-hydroxy-5-hydroxy-5-azacytidine, N4-hydroxy-5-methylpseudoisocytidine, N4-hydroxy-5-aminopseudoisocytidine, N4-hydroxy-5-hydroxypseudoisocytidine, 2-thio-N4-methyl-5-methylcytidine, 2-thio-N4-methyl-5-aminocytidine, 2-thio-N4-methyl-5-hydroxycytidine, 2-thio-N4-methyl-5-methyl-5-azacytidine, 2-thio-N4-methyl-5-amino-5-azacytidine, 2-thio-N4-methyl-5-hydroxy-5-azacytidine, 2-thio-N4-methyl-5-methylpseudoisocytidine, 2-thio-N4-methyl-5-aminopseudoisocytidine, 2-thio-N4-methyl-5-hydroxypseudoisocytidine, 2-thio-N4-amino-5-azacytidine, 2-thio-N4-aminopseudoisocytidine, 2-thio-N4-amino-5-methylcytidine, 2-thio-N4-amino-5-aminocytidine, 2-thio-N4-amino-5-hydroxycytidine, 2-thio-N4-amino-5-methyl-5-azacytidine, 2-thio-N4-amino-5-amino-5-azacytidine, 2-thio-N4-amino-5-hydroxy-5-azacytidine, 2-thio-N4-amino-5-methylpseudoisocytidine, 2-thio-N4-amino-5-aminopseudoisocytidine, 2-thio-N4-amino-5-hydroxypseudoisocytidine, 2-thio-N4-hydroxy-5-azacytidine, 2-thio-N4-hydroxypseudoisocytidine, 2-thio-N4-hydroxy-5-methylcytidine, N4-hydroxy-5-aminocytidine, 2-thio-N4-hydroxy-5-hydroxycytidine, 2-thio-N4-hydroxy-5-methyl-5-azacytidine, 2-thio-N4-hydroxy-5-amino-5-azacytidine, 2-thio-N4-hydroxy-5-hydroxy-5-azacytidine, 2-thio-N4-hydroxy-5-methylpseudoisocytidine, 2-thio-N4-hydroxy-5-aminopseudoisocytidine, 2-thio-N4-hydroxy-5-hydroxypseudoisocytidine, N6-methyladenosine, N6-aminoadenosine, N6-hydroxyadenosine, 7-deazaadenosine, 8-azaadenosine, N6-methyl-7-deazaadenosine, N6-methyl-8-azaadenosine, 7-deaza-8-azaadenosine, N6-methyl-7-deaza-8-azaadenosine, N6-amino-7-deazaadenosine, N6-amino-8-azaadenosine, N6-amino-7-deaza-8-azaadenosine, N6-hydroxyadenosine, N6-hydroxy-7-deazaadenosine, N6-hydroxy-8-azaadenosine, N6-hydroxy-7-deaza-8-azaadenosine, 6-thioguanosine, 7-deazaguanosine, 8-azaguanosine, 6-thio-7-deazaguanosine, 6-thio-8-azaguanosine, 7-deaza-8-azaguanosine, and 6-thio-7-deaza-8-azaguanosine.

In embodiments, the compound, pharmaceutical composition, or lipid aggregate described herein is complexed with or associates with a nucleic acid (e.g. DNA or RNA, e.g. mRNA) and the nucleic acid encodes a protein of interest. In embodiments, the protein of interest is a soluble protein. In embodiments, the protein of interest is one or more of a reprogramming protein and a gene-editing protein.

This invention is further illustrated by the following non-limiting examples.

EXAMPLES

Example 1: Synthesis of Linoleoyl Chloride (1)

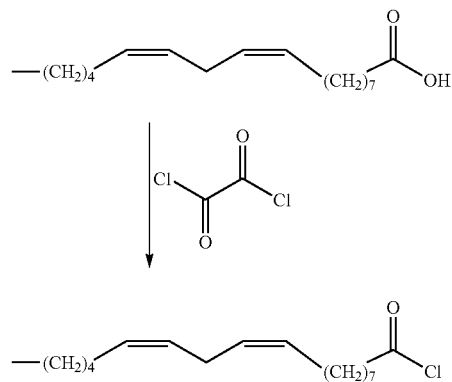

Oxalyl chloride (47.0 mL, 555 mmol) was added to a solution of linoleic acid (70.0 g, 250 mmol) in 580 mL anhydrous methylene chloride at 0° C. under $N_2$ atmosphere. The reaction was warmed to room temperature and stirred vigorously for 24 hours. Solvent and oxalyl chloride were removed under reduced pressure to yield linoleoyl chloride as a brown oil, which was used without further purification.

Example 2: Synthesis of N1,N4-dilinoleoyl-diaminobutane (2)

A solution of 1,4-diaminobutane (0.428 g, 4.86 mmol) and triethylamine (2.03 mL, 14.6 mmol) in 1 mL of anhydrous methylene chloride was slowly added to a solution of linoleoyl chloride (2.98 g, 10.0 mmol) in 30 mL of anhydrous methylene chloride in an ice bath at 0° C. The reaction mixture was stirred vigorously with a magnetic stir bar. After addition was complete, the ice bath was removed and the mixture was stirred at room temperature for 2.5 days. The reaction was cooled to 4° C., and a white solid precipitated from the solution. The excess linoleoyl chloride was removed by vacuum filtration. The precipitate was washed twice with 10 mL of methylene chloride. The mother liquor was concentrated and more product precipitated. This precipitate was filtered and combined with the previous precipitate. The resulting solid was vacuum dried for 4 hours. A total of 1.9 g of a white solid of the desired product, $N^1,N^4$-dilinoleoyl-diaminobutane, was obtained.

Example 3: Synthesis of N1,N4-dilinoleyl-diaminobutane (3)

Lithium aluminum hydride (0.6 g, 95%, 16 mmol) was carefully added to a suspension of $N^1,N^4$-dilinoleoyl-diaminobutane (1.8 g, 2.9 mmol) in 50 mL anhydrous diethyl ether at 0° C. After addition was complete, the ice bath was removed. The reaction mixture was warmed slowly to room temperature and then heated gently to reflux with an appropriate condensing device and stirred for 12 hours. The reaction mixture was cooled and quenched carefully at 0° C. with 5 mL of water. The diethyl ether was removed under reduced pressure, and the reaction mixture was dried under vacuum. The dried reaction mixture was extracted three times with 25 mL of isopropyl alcohol at 80° C. The isopropyl alcohol was removed to yield 1.6 g of oily colorless $N^1,N^4$-dilinoleyl-diaminobutane.

Example 4: Synthesis of N1,N4-dilinoleyl-N1,N4-di-[2-hydroxy-3-(N-phthalamido)propyl]-diaminobutane (4)

Diisopropylethylamine (1.15 mL, 12.0 mmol) was added to a suspension of $N^1,N^4$-dilinoleyl-diaminobutane (1.6 g, 2.7 mmol) and N-(2,3-epoxypropyl)-phthalimide (1.6 g, 7.9 mmol) in 12 mL of dry N,N-dimethylformamide. After purging with nitrogen, the reaction mixture was sealed in a round-bottom flask and heated to around 90° C. for 24 hours. N,N-dimethylformamide and diisopropylethylamine were removed and a yellow oil was obtained. Synthesis was continued without additional purification.

Example 5: Synthesis of N1,N4-dilinoleyl-N1,N4-di-(2-hydroxy-3-aminopropyl)-diaminobutane (5)

Figure 9A:
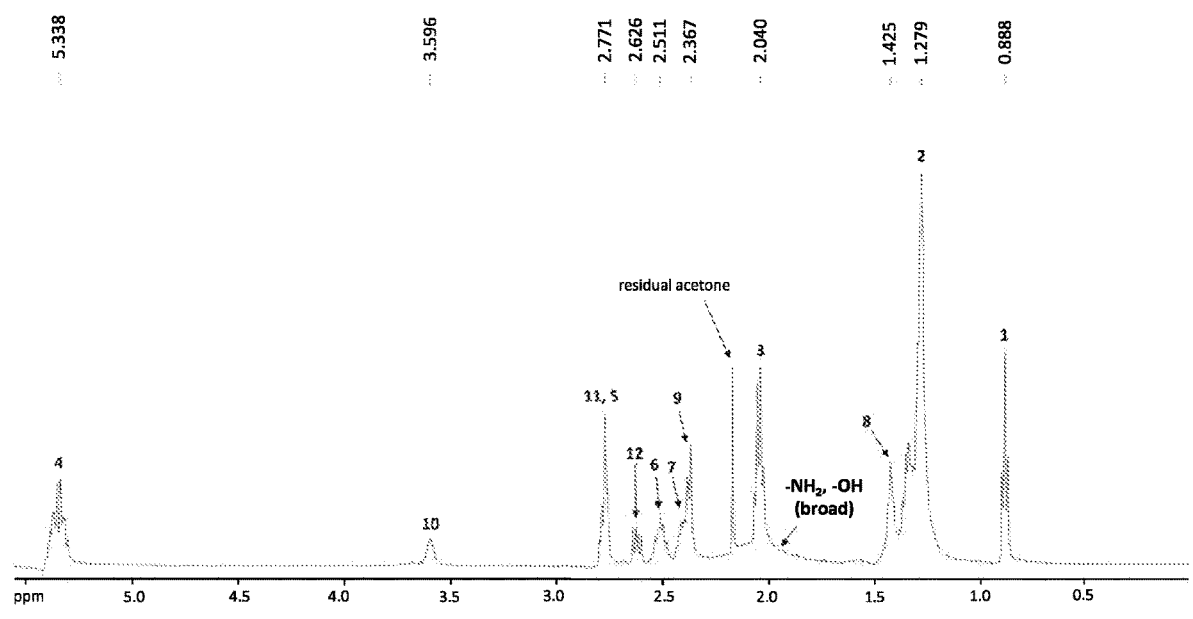
FIG. 9A depicts the measured 500 MHz proton NMR spectrum of DHDLinS in deuterated chloroform.
Figure 9B:
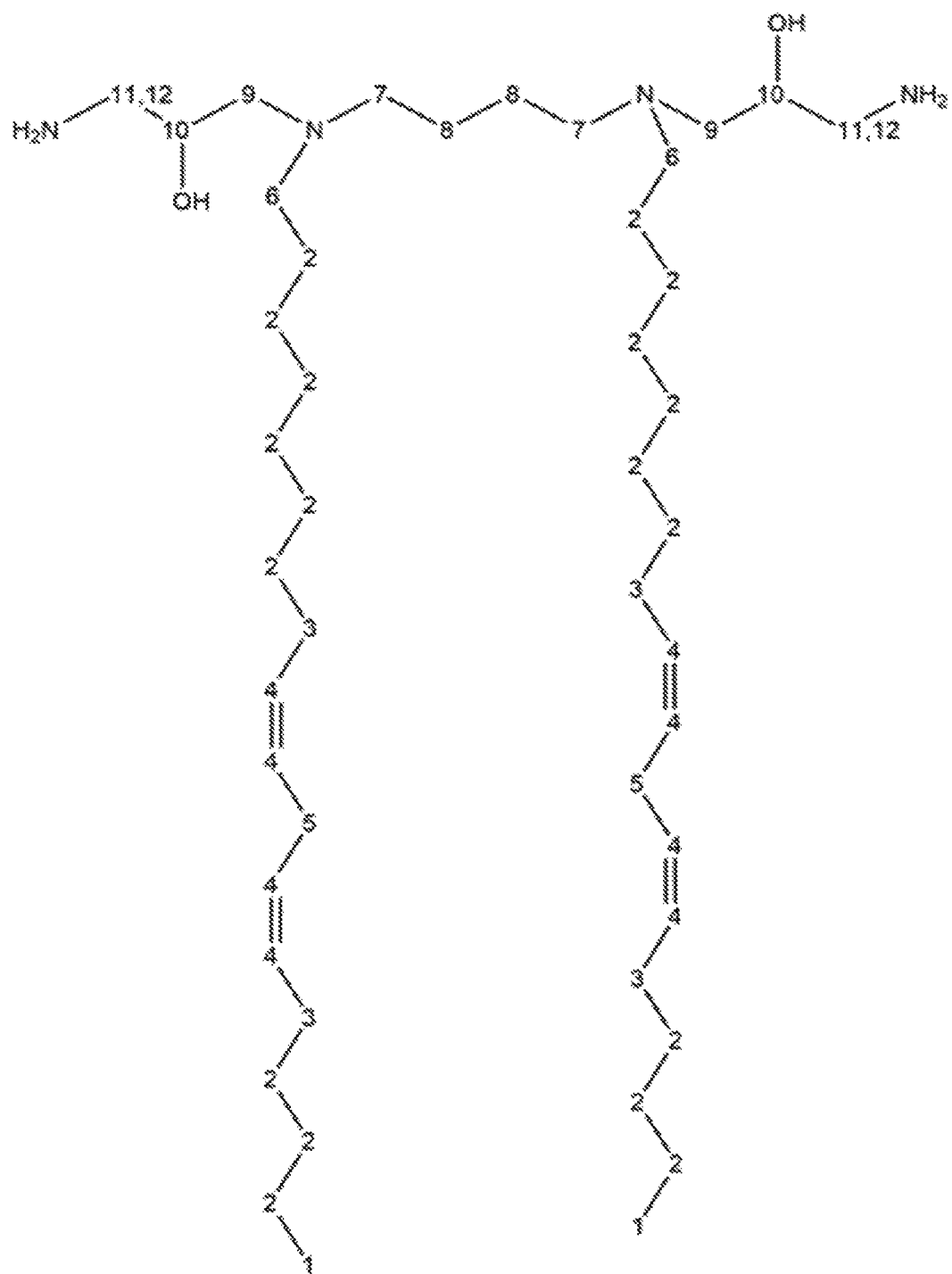
FIG. 9B depicts DHDLinS.

The entire crude oil of $N^1,N^4$-dilinoleyl-$N^1,N^4$-di-[2-hydroxy-3-(N-phthalamido)propyl]-diaminobutane was dissolved in 25 mL of anhydrous ethanol. Hydrazine (0.5 mL, 64-65% aq., 10.3 mmol) was added at room temperature. With an appropriate condensing device, the reaction mixture was heated to reflux. The oil bath was set to 85° C. After 15 minutes, a white solid precipitated from the solution. The reaction mixture was stirred at reflux for 4 hours before being cooled to −20° C. The white solid was removed by gravity filtration. The residue was washed twice with cold ethanol. The combined ethanol solution was concentrated and dried overnight under vacuum. The crude product was extracted with acetone. The combined acetone solution was concentrated and dried overnight under vacuum. 1.0 g of an oil, $N^1,N^4$-dilinoleyl-$N^1,N^4$-di-(2-hydroxy-3-aminopropyl)-diaminobutane (referred to herein as DHDLinS, see FIG. 9B), was obtained. The proton NMR spectrum of a 1-2 mg sample of DHDLinS in 0.6 mL deuterated chloroform was measured on a 500 MHz Varian Inova instrument (FIG. 9A).

Example 6: Synthesis of Lipids

The following compounds were synthesized by the methods of Examples 1 through 5 using the corresponding amine:
$N^1,N^4$-dilinoleyl-$N^1,N^4$-di-(2-hydroxy-3-aminopropyl)-diaminobutane (6);
$N^1,N^2$-dilinoleyl-$N^1,N^2$-di-(2-hydroxy-3-aminopropyl)-diaminoethane (7);
$N^1,N^3$-dilinoleyl-$N^1,N^3$-di-(2-hydroxy-3-aminopropyl)-diaminopropane (8);
$N^1,N^5$-dilinoleyl-$N^1,N^5$-di-(2-hydroxy-3-aminopropyl)-diaminopentane (9);
$N^1,N^6$-dilinoleyl-$N^1,N^6$-di-(2-hydroxy-3-aminopropyl)-diaminohexane (10);
$N^1,N^8$-dilinoleyl-$N^1,N^8$-di-(2-hydroxy-3-aminopropyl)-diaminooctane (11);
$N^1,N^{10}$-dilinoleyl-$N^1,N^{10}$-di-(2-hydroxy-3-aminopropyl)-diaminodecane (12);
$N^1,N^{12}$-dilinoleyl-$N^1,N^{12}$-di-(2-hydroxy-3-aminopropyl)-diaminododecane (13).

Example 7: Transfection with Inventive Lipids

Stock solutions of lipid in ethanol were prepared at concentrations of between 5 mg/mL and 20 mg/mL and stored at −20° C. To perform transfections, nucleic acid was first diluted in DMEM (1 µg of nucleic acid in 50 µL of DMEM), then the desired amount of lipid stock solution was added. After adding the lipid, the solution was mixed thoroughly, and complexes were allowed to form for between about 5 minutes and about 25 minutes before adding to cells. For the experiments depicted in FIG. 1 through FIG. 6, the lipid was used without the acetone purification described in Example 5.

FIG. 1 depicts transfection of primary human epidermal keratinocytes with in vitro transcribed RNA encoding green fluorescent protein (GFP) complexed with the indicated lipids. As shown in the figure, cells were transfected with high efficiency by DHDLinS.

Figure 2:
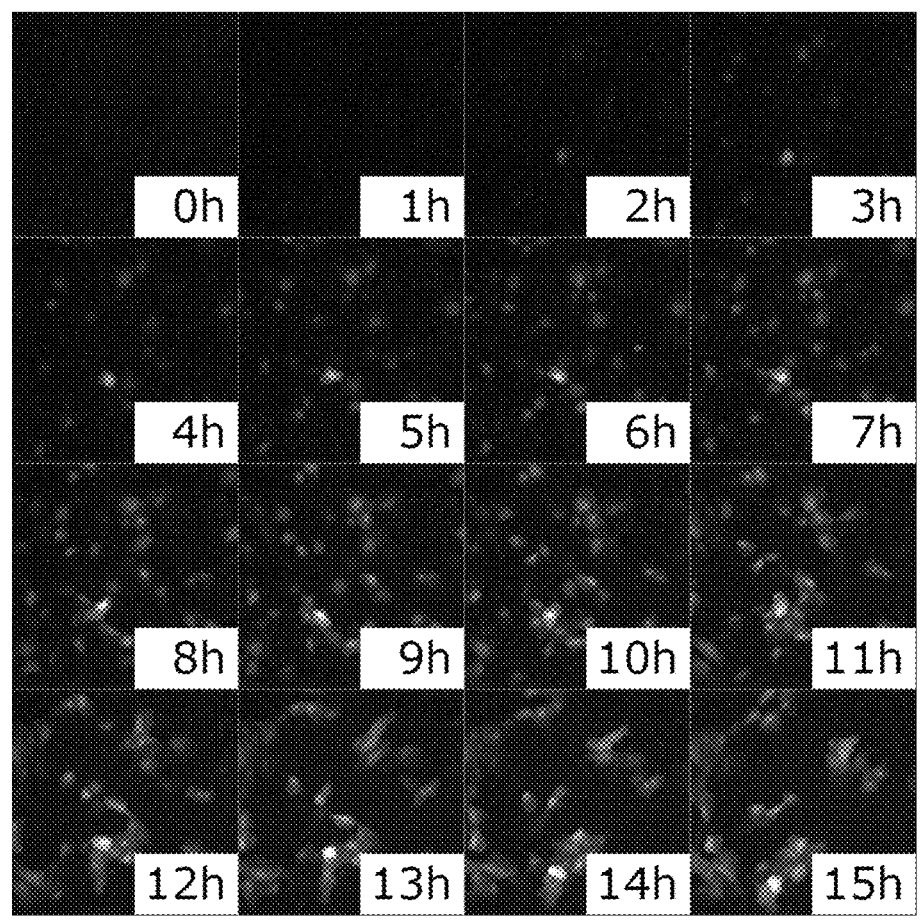

FIG. 2 depicts a time course of the experiment of FIG. 1, i.e. florescence measured at the indicated time points following transfection using DHDLinS. A fluorescent signal was detected one hour following transfection, and both the signal intensity and number of fluorescent cells increased for several hours following transfection.

Figure 3:
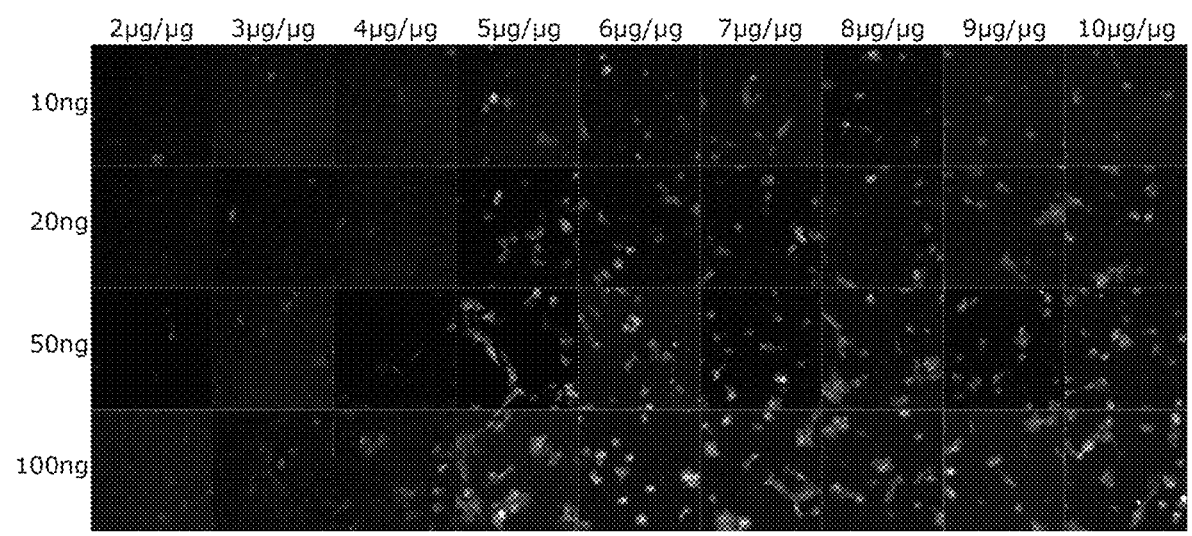

FIG. 3 depicts transfection with various indicated amounts of RNA (in nanograms) and lipid-to-RNA mass ratios (in micrograms of lipid per microgram of RNA). As shown in the figure, all RNA amounts and lipid-to-RNA mass ratios tested yielded a fluorescent signal. In general, larger amounts of RNA yielded a stronger signal and/or larger number of fluorescent cells, while minimal increase in fluorescence signal was observed at lipid-to-RNA mass ratios greater than 5 µg/µg.

Figure 4:
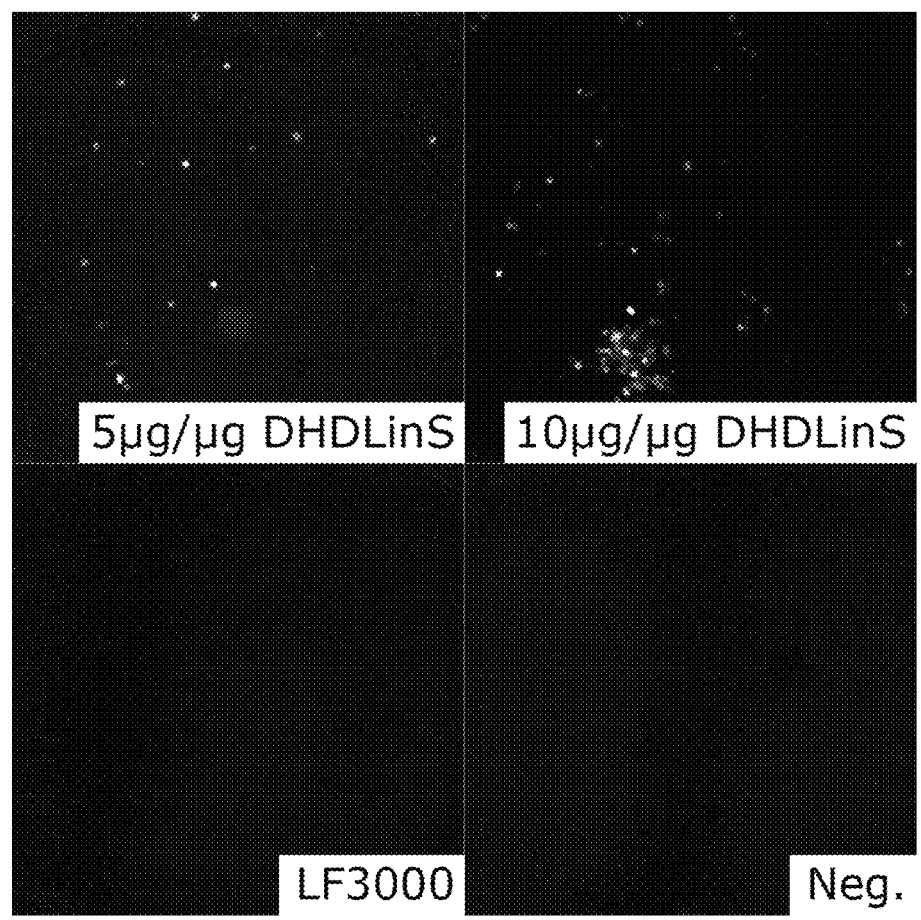
FIG. 4 depicts the results of an experiment conducted as in FIG. 1, but with human peripheral blood mononuclear cells (hPBMCs) instead of keratinocytes. Images were taken 16 hours following transfection. "LF3000" indicates cells transfected with LIPOFECTAMINE 3000 (cationic liposome formulation) commercial transfection reagent. "Neg." indicates un-transfected cells.

FIG. 4 depicts a transfection experiment with human peripheral blood mononuclear cells (hPBMCs) instead of keratinocytes. As shown in the figure, DHDLinS effectively transfected hPBMCs at both lipid-to-RNA mass ratios tested, while no transfection was observed with LIPOFECTAMINE 3000, (cationic liposome formulation, "LF3000") a commercial transfection reagent.

Figure 5A:
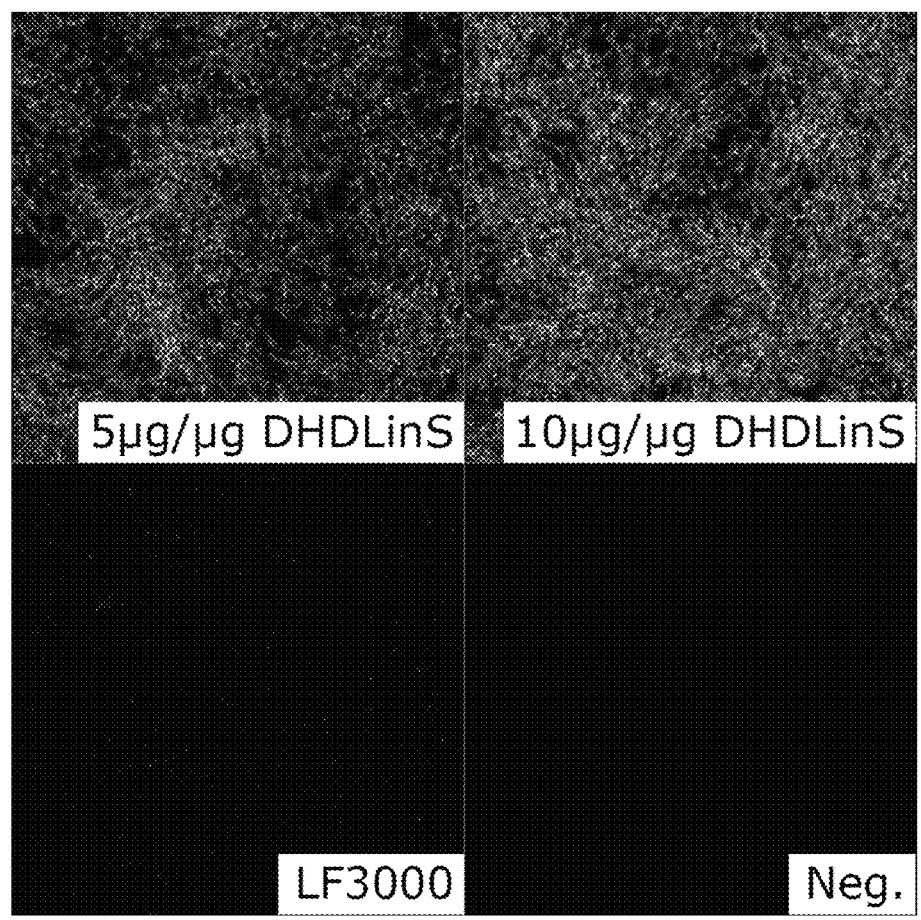
FIG. 5A depicts the results of an experiment conducted as in FIG. 4, but with a confluent layer of primary human epidermal keratinocytes instead of hPBMCs. Images were taken 24 hours following transfection.
Figure 5B:
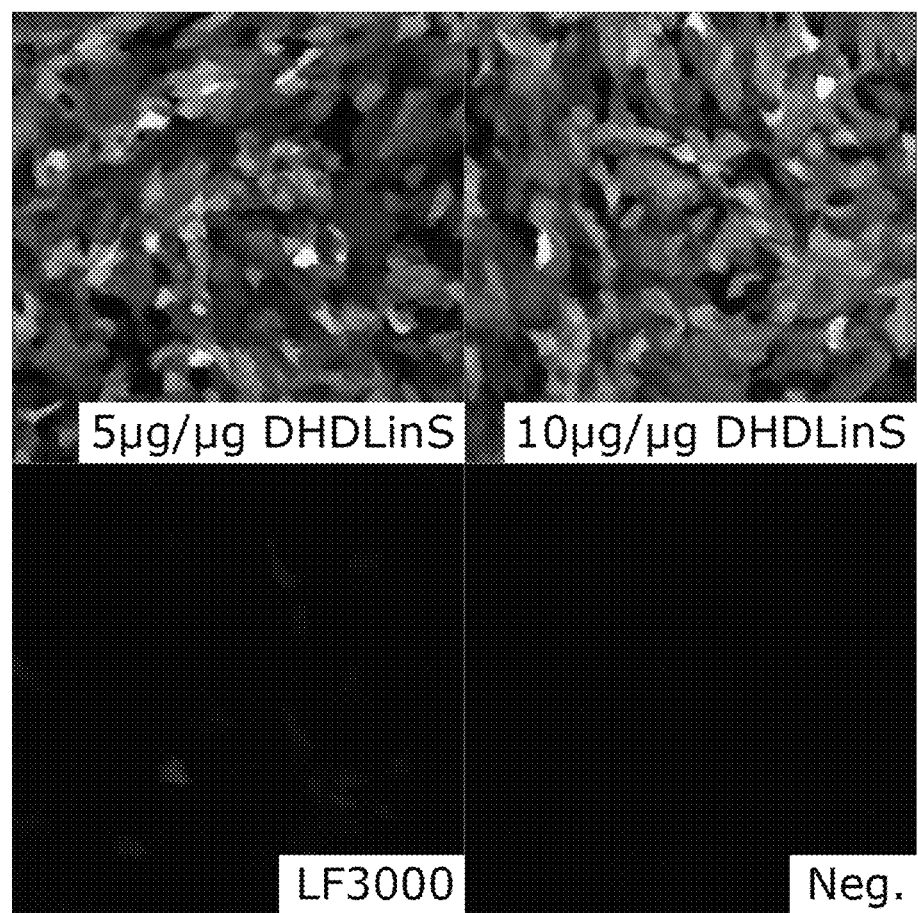
FIG. 5B depicts the experiment of FIG. 5A, shown at higher magnification.

FIG. 5A extends the transfection findings to a confluent layer of primary human epidermal keratinocytes instead of hPBMCs. As shown in the figure, DHDLinS effectively transfected confluent primary human epidermal keratinocytes at both lipid-to-RNA mass ratios tested, while the cells treated with LIPOFECTAMINE 3000 (cationic liposome formulation) were not efficiently transfected. FIG. 5B depicts this at higher magnification. As shown in the figure, DHDLinS effectively transfected confluent primary human epidermal keratinocytes at both lipid-to-RNA mass ratios tested, while the cells treated with LIPOFECTAMINE 3000 (cationic liposome formulation) were not efficiently transfected.

Figure 6A:
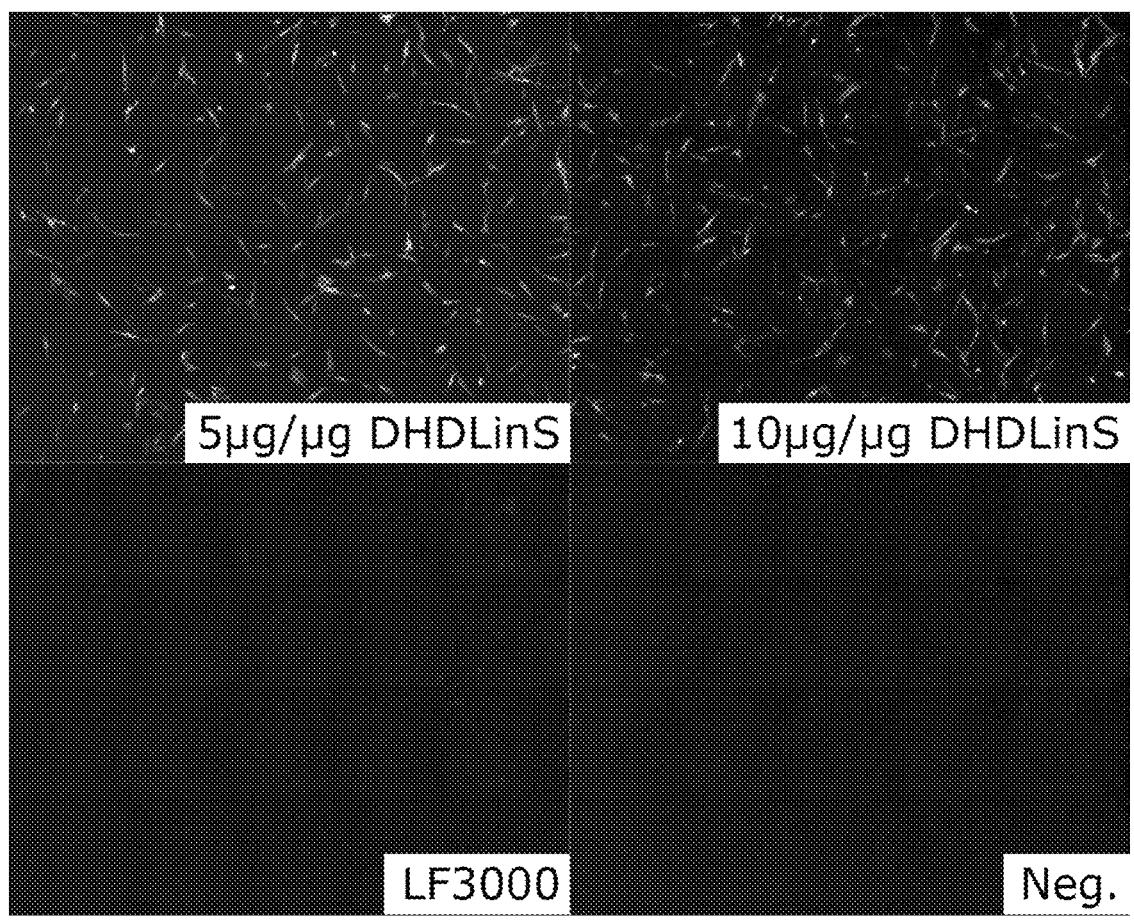
FIG. 6A depicts the results of an experiment conducted as in FIG. 4, but with primary human adult dermal fibroblasts instead of hPBMCs. Images were taken 16 hours following transfection.
Figure 6B:
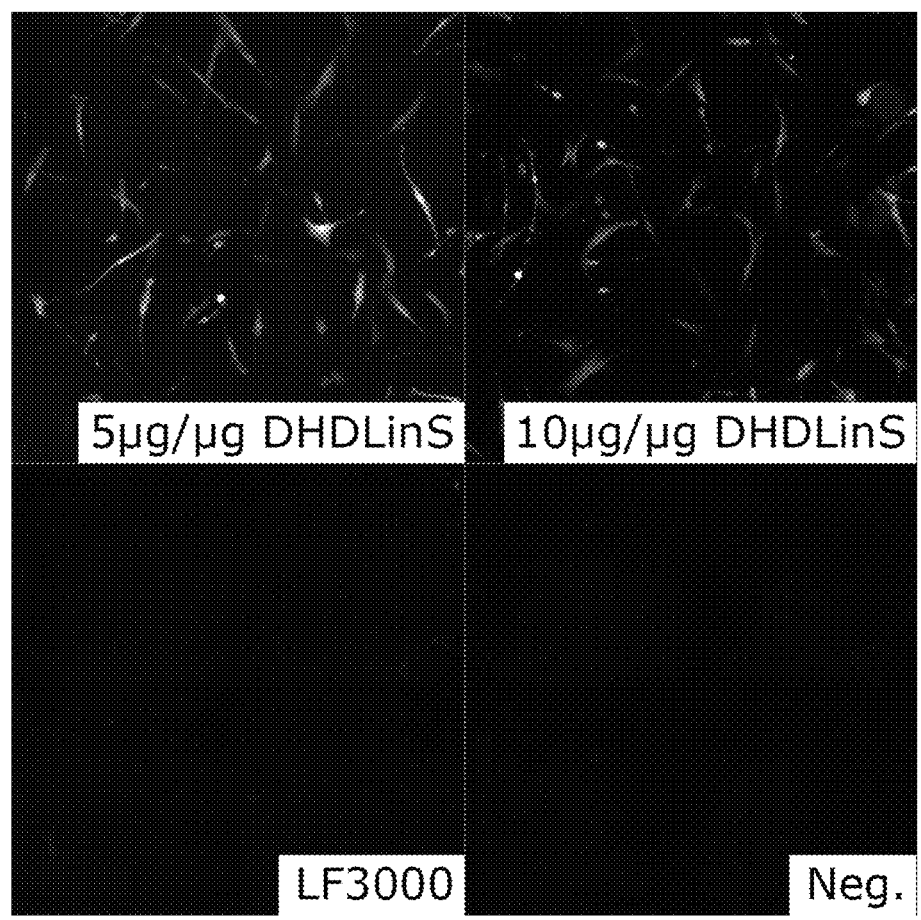
FIG. 6B depicts the experiment of FIG. 6A, shown at higher magnification.

FIG. 6A depicts the results of an experiment conducted as in FIG. 4, but with primary human adult dermal fibroblasts instead of hPBMCs. As shown in the figure, DHDLinS effectively transfected primary human adult dermal fibroblasts at both lipid-to-RNA mass ratios tested, while the cells treated with LIPOFECTAMINE 3000 (cationic liposome formulation) were not efficiently transfected. FIG. 6B depicts this experiment at higher magnification. As shown in the figure, DHDLinS effectively transfected primary human adult dermal fibroblasts at both lipid-to-RNA mass ratios tested, while the cells treated with LIPOFECTAMINE 3000 (cationic liposome formulation) were not efficiently transfected.

Figure 7:
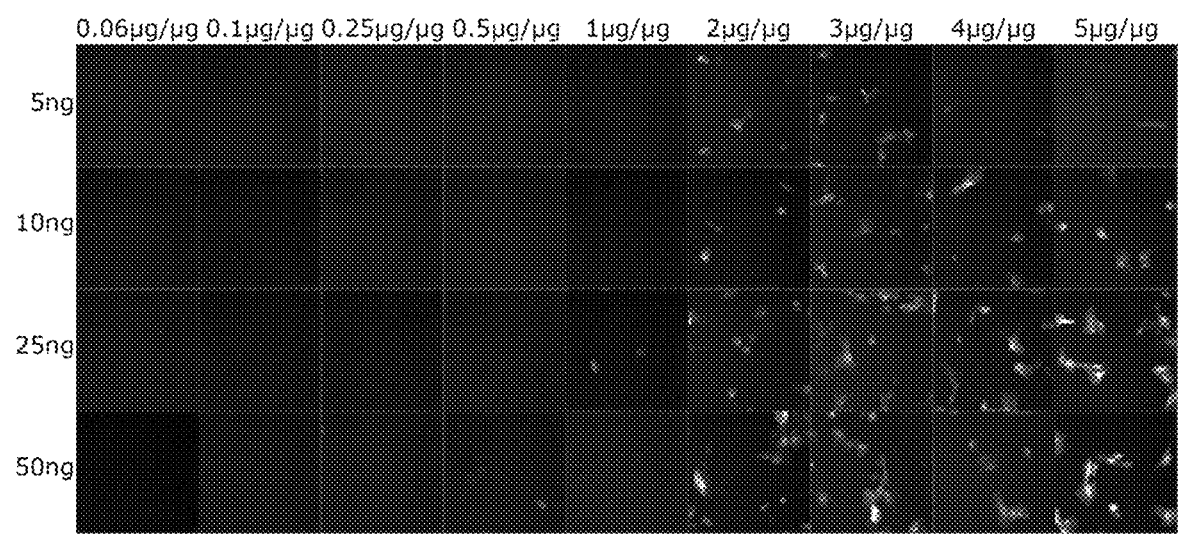
FIG. 7 depicts the results of an experiment conducted as in FIG. 3, but with DHDLinS purified by extraction with acetone as described in Example 5.

FIG. 7 depicts the results of an experiment conducted as in FIG. 3, but with DHDLinS purified by extraction with acetone as described in Example 5. As shown in the figure, minimal increase in fluorescence signal was observed at lipid-to-RNA mass ratios greater than 2 µg/µg.

Figure 8:
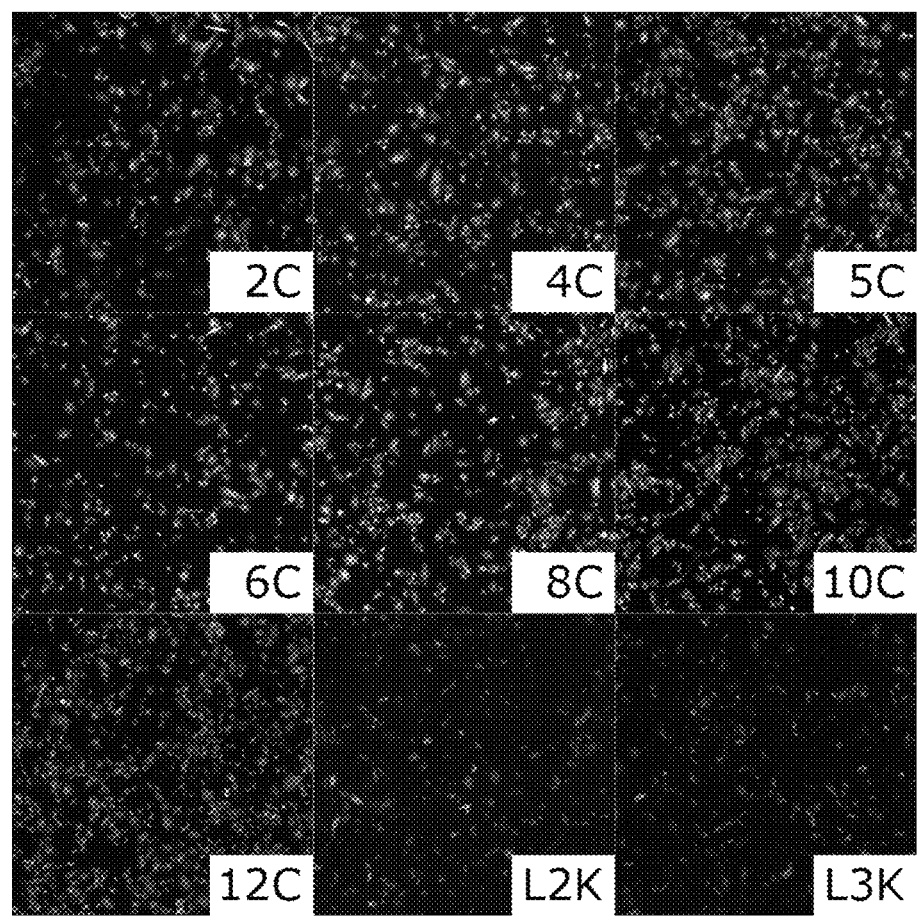
FIG. 8 depicts primary human epidermal keratinocytes cultured in a 24-well plate, and transfected with 100 ng per well of in vitro transcribed RNA encoding green fluorescent protein (GFP) complexed with the compounds of Formula I, where n is as indicated. Images were taken eight hours following transfection.

FIG. 8 depicts primary human epidermal keratinocytes cultured in a 24-well plate, and transfected with 100 ng per well of in vitro transcribed RNA encoding green fluorescent protein (GFP) complexed with the compounds of Formula I, where n is as indicated or with LIPOFECTAMINE 2000 (cationic liposome formulation, "L2K") or LIPO-FECTAMINE 3000 (cationic liposome formulation, "L3K"). Images were taken eight hours following transfection.

TABLE 1

Transfection with Inventive Lipids

| Transfection reagent | Fluorescence Intensity |
| --- | --- |
| Formula I (n = 2) | 6623 |
| Formula I (n = 4), a.k.a. "DHDLinS" | 8009 |
| Formula I (n = 5) | 7554 |
| Formula I (n = 6) | 8596 |
| Formula I (n = 8) | 9170 |
| Formula I (n = 10) | 7842 |
| Formula I (n = 12) | 5631 |
| LIPOFECTAMINE 2000 (cationic liposome formulation) | 3356 |
| LIPOFECTAMINE 3000 (cationic liposome formulation) | 3157 |

Table 1 depicts the results of an experiment in which 20,000 neonatal human epidermal keratinocytes (HEKn) per well of a 24-well plate were transfected with 100 ng of in vitro transcribed RNA encoding green fluorescent protein (GFP) complexed with the indicated lipids. Fluorescence was measured 24 hours after transfection. Numbers indicate mean fluorescence intensity per cell (a.u.).

EQUIVALENTS

Those skilled in the art will recognize, or be able to ascertain, using no more than routine experimentation, numerous equivalents to the specific embodiments described specifically herein. Such equivalents are intended to be encompassed in the scope of the following claims.

INCORPORATION BY REFERENCE

All patents and publications referenced herein are hereby incorporated by reference in their entireties.

What is claimed is:

1. A compound of the formula:

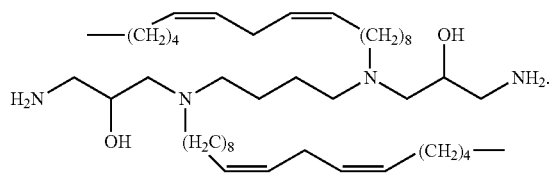

2. A pharmaceutical composition comprising the compound of claim 1.
3. A lipid aggregate comprising the compound of claim 1.
4. A lipid nanoparticle comprising the compound of claim 1.
5. A liposome comprising the compound of claim 1.
6. A lipid carrier comprising the compound of claim 1.
7. A composition comprising the compound of claim 1, and a nucleic acid.
8. The composition of claim 7, wherein the nucleic acid comprises DNA.
9. The composition of claim 7, wherein the nucleic acid comprises RNA.
10. The composition of claim 7, wherein the nucleic acid is an in vitro transcribed mRNA.
11. The composition of claim 10, wherein the in vitro transcribed mRNA comprises a non-canonical nucleotide.
12. The composition of claim 7, wherein the nucleic acid is an siRNA.
13. The composition of claim 7, wherein the nucleic acid is an antisense oligonucleotide.
14. The pharmaceutical composition of claim 2, further comprising an additional lipid.
15. The lipid aggregate of claim 3, further comprising an additional lipid.
16. The lipid nanoparticle of claim 4, further comprising an additional lipid.
17. The liposome of claim 5, further comprising an additional lipid.
18. The lipid carrier of claim 6, further comprising an additional lipid.
19. The composition of claim 7, further comprising an additional lipid.
20. The composition of claim 9, further comprising an additional lipid.
21. The composition of claim 10, further comprising an additional lipid.
22. The pharmaceutical composition of claim 14, wherein the additional lipid is selected from dioleoylphosphatidylethanolamine (DOPE), 1,2-Dioleoyl-sn-glycero-3-phosphocholine (DOPC), cholesterol, and a polyethylene glycol (PEG)-modified lipid.
23. The lipid aggregate of claim 15, wherein the additional lipid is selected from dioleoylphosphatidylethanolamine (DOPE), 1,2-Dioleoyl-sn-glycero-3-phosphocholine (DOPC), cholesterol, and a polyethylene glycol (PEG)-modified lipid.
24. The lipid nanoparticle of claim 16, wherein the additional lipid is selected from dioleoylphosphatidylethanolamine (DOPE), 1,2-Dioleoyl-sn-glycero-3-phosphocholine (DOPC), cholesterol, and a polyethylene glycol (PEG)-modified lipid.
25. The liposome of claim 17, wherein the additional lipid is selected from dioleoylphosphatidylethanolamine (DOPE), 1,2-Dioleoyl-sn-glycero-3-phosphocholine (DOPC), cholesterol, and a polyethylene glycol (PEG)-modified lipid.
26. The lipid carrier of claim 18, wherein the additional lipid is selected from dioleoylphosphatidylethanolamine (DOPE), 1,2-Dioleoyl-sn-glycero-3-phosphocholine (DOPC), cholesterol, and a polyethylene glycol (PEG)-modified lipid.
27. The composition of claim 19, wherein the additional lipid is selected from dioleoylphosphatidylethanolamine (DOPE), 1,2-Dioleoyl-sn-glycero-3-phosphocholine (DOPC), cholesterol, and a polyethylene glycol (PEG)-modified lipid.
28. The composition of claim 20, wherein the additional lipid is selected from dioleoylphosphatidylethanolamine (DOPE), 1,2-Dioleoyl-sn-glycero-3-phosphocholine (DOPC), cholesterol, and a polyethylene glycol (PEG)-modified lipid.
29. The composition of claim 21, wherein the additional lipid is selected from dioleoylphosphatidylethanolamine (DOPE), 1,2-Dioleoyl-sn-glycero-3-phosphocholine (DOPC), cholesterol, and a polyethylene glycol (PEG)-modified lipid.
30. The composition of claim 11, further comprising an additional lipid or helper, wherein the additional or helper lipid is selected from dioleoylphosphatidylethanolamine (DOPE), 1,2-Dioleoyl-sn-glycero-3-phosphocholine (DOPC), cholesterol, and a polyethylene glycol (PEG)-modified lipid.

\* \* \* \* \*